US009155783B2

(12) United States Patent
Leclerc et al.

(10) Patent No.: US 9,155,783 B2
(45) Date of Patent: Oct. 13, 2015

(54) AGENTS AND METHODS BASED ON THE USE OF THE EDA DOMAIN OF FIBRONECTIN

(75) Inventors: Claude Leclerc, Navarra (ES); Juan Jose Lasarte Sagastibelza, Navarra (ES); Marta Gorraiz Ayala, Navarra (ES); Jesus Prieto Valtuena, Navarra (ES)

(73) Assignee: PROYECTO DE BIOMEDICINA CIMA, S.L., Navarra (ES)

( * ) Notice: Subject to any disclaimer, the term of this patent is extended or adjusted under 35 U.S.C. 154(b) by 1724 days.

(21) Appl. No.: 11/922,148

(22) PCT Filed: Jun. 13, 2006

(86) PCT No.: PCT/ES2006/000343
§ 371 (c)(1),
(2), (4) Date: Jun. 16, 2008

(87) PCT Pub. No.: WO2006/134190
PCT Pub. Date: Dec. 21, 2006

(65) Prior Publication Data
US 2009/0220532 A1  Sep. 3, 2009

(30) Foreign Application Priority Data
Jun. 13, 2005 (ES) .................................. 200501412

(51) Int. Cl.
| | | |
|---|---|---|
| *A61K 6/00* | (2006.01) | |
| *A61K 38/00* | (2006.01) | |
| *A61K 38/16* | (2006.01) | |
| *A61K 38/17* | (2006.01) | |
| *A61K 38/38* | (2006.01) | |
| *A61K 38/39* | (2006.01) | |
| *A61K 39/00* | (2006.01) | |
| *C07K 1/00* | (2006.01) | |
| *C07K 14/00* | (2006.01) | |
| *C07K 14/435* | (2006.01) | |
| *C07K 14/78* | (2006.01) | |

(52) U.S. Cl.
CPC .............. *A61K 38/39* (2013.01); *A61K 39/0011* (2013.01); *C07K 14/78* (2013.01); *C07K 2319/33* (2013.01); *C07K 2319/40* (2013.01); *C12N 2770/24211* (2013.01)

(58) Field of Classification Search
CPC ......... A61K 6/00; A61K 38/00; A61K 38/16; A61K 38/17; A61K 38/38; A61K 38/39; A61K 39/00; A61K 39/0005; A61K 39/0011; C07K 1/00; C07K 14/00; C07K 14/435; C07K 14/76; C07K 14/78; C07K 2316/00; C07K 2319/00; C07K 2319/20; C07K 2319/33; C07K 2319/40; C12N 2710/00; C12N 2770/00; C12N 2770/00011; C12N 2770/24
See application file for complete search history.

(56) References Cited

U.S. PATENT DOCUMENTS

| | | | |
|---|---|---|---|
| 5,108,898 A | 4/1992 | Peters et al. | |
| 2006/0024724 A1* | 2/2006 | Hussa et al. | ...................... 435/6 |
| 2006/0134065 A1* | 6/2006 | Fournillier | ................... 424/93.2 |

FOREIGN PATENT DOCUMENTS

| | | |
|---|---|---|
| EP | 1 188 446 | 3/2002 |
| WO | 00/76456 | 12/2000 |
| WO | 03/070761 | 8/2003 |

OTHER PUBLICATIONS

International Search Report issued in Dec. 20, 2006 in the International (PCT) Application of which the present application is the U.S. National Stage.
Y. Okamura et al., "The Extra Domain A of Fibronectin Activates Toll-Like Receptor 4", The Journal of Biological Chemistry, vol. 276, No. 13, pp. 10229-10233, Mar. 30, 2001.
G. Paolella et al., "Sequence Analysis and in Vivo Expression Show that Alternative Splicing of ED-B and ED-A Regions of the Human Fibronectin Gene are Independent Events", Nucleic Acids Research, vol. 16, No. 8, Apr. 1988.
T. Kaisho et al., "Toll-Like Receptors as Adjuvant Receptors", Biochimica et Biophysica Acta, vol. 1589, No. 1, pp. 1-13, Feb. 2002.
A. F. Muro et al., "Regulation of the Fibronectin EDA Exon Alternative Splicing. Cooperative Role of the Exonic Enhancer Element and the 5' Splicing Site", FEBS Letters, vol. 437, Nos. 1-2, pp. 137-141, 1998.
M. B. Lutz et al., "Immature, Semi-Mature and Fully Mature Dendritic Cells: Which Signals Induce Tolerance or Immunity", Trends in Immunology, vol. 23, No. 9, pp. 445-449, Sep. 2002.
P. Martin et al., "Genetic Immunization and Comprehensive Screening Approaches in HLA-A2 Transgenic Mice Lead to the Identification of Three Novel Epitopes in Hepatitis C Virus NS3 Antigen", Journal of Medical Virology, vol. 74, No. 3, pp. 397-405, Nov. 2004.
Shigeki Saito, et al., "The Fibronectin Extra Domain A Activates Matrix Metalloproteinase Gene Expression by an Interleukin-1-dependent Mechanism", The Journal of Biological Chemistry, vol. 274, No. 43, Oct. 22, 1999, pp. 30756-30763.
Yoshinori Okamura, et al., "The Extra Domain A of Fibronectin Activates Toll-like Receptor 4", The Journal of Biological Chemistry, vol. 276, No. 13, Mar. 30, 2001, pp. 10229-10233.

(Continued)

*Primary Examiner* — Alana Harris Dent
(74) *Attorney, Agent, or Firm* — Wenderoth, Lind & Ponack, L.L.P.

(57) ABSTRACT

This invention relates to the use of a polypeptide in the production of an immunostimulatory agent, said polypeptide comprising a sequence corresponding to the EDA domain of fibronectin, a fragment of the EDA domain which can bind to TLR4 or a variant of said EDA domain or a fragment which can bind to TLR4 and which has a homology of more than 70% with any form or natural fragment of the EDA domain. The invention also relates to the production methods and applications of said agent.

25 Claims, 10 Drawing Sheets

(56) References Cited

OTHER PUBLICATIONS

Giovanni Paolella, et al., "Sequence analysis and in vivo expression show that alternative splicing of ED-B and ED-A regions of the human fibronectin gene are independent events", Nucleic Acids Research, vol. 16, No. 8, 1988, pp. 3545-3557.

Tsuneyasu Kaisho, et al., "Toll-like receptors as adjuvant receptors", Biochimica et Biophysica Acta, 2002, pp. 1-13.

A.F. Muro, et al., "Regulation of the fibronectin EDA exon alternative splicing. Cooperative role of the exonic enhancer element and the 5' splicing site", FEBS letters, vol. 437, 1998, pp. 137-141.

Manfred B. Lutz, et al., "Immature, semi-mature and fully mature dendritic cells: which signals induce tolerance or immunity", Trends in Immunology, vol. 23, No. 9, Sep. 2002, pp. 445-449.

* cited by examiner

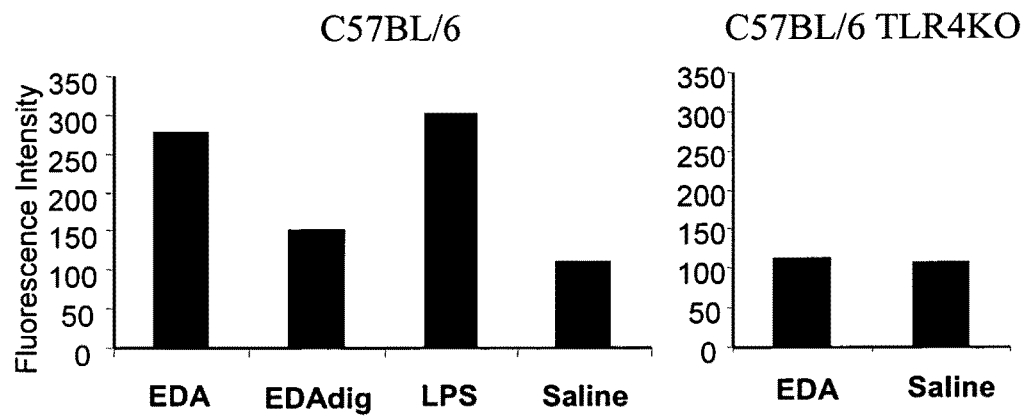
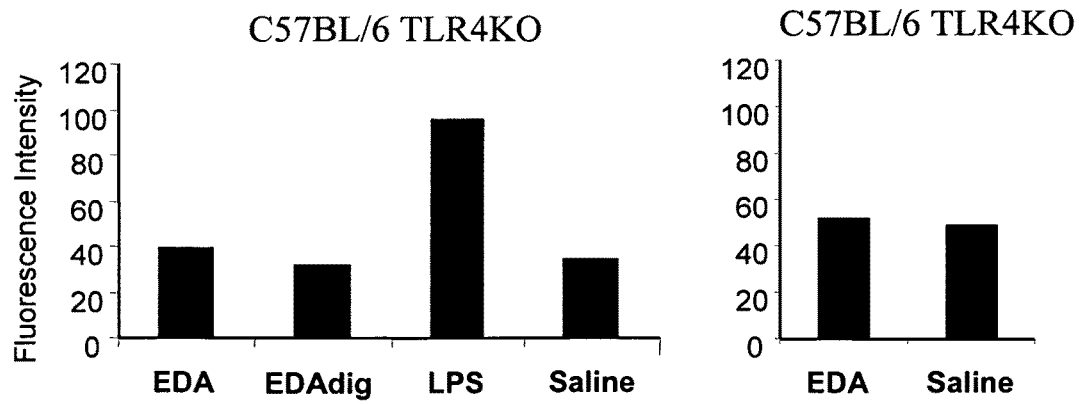
Figure 5B

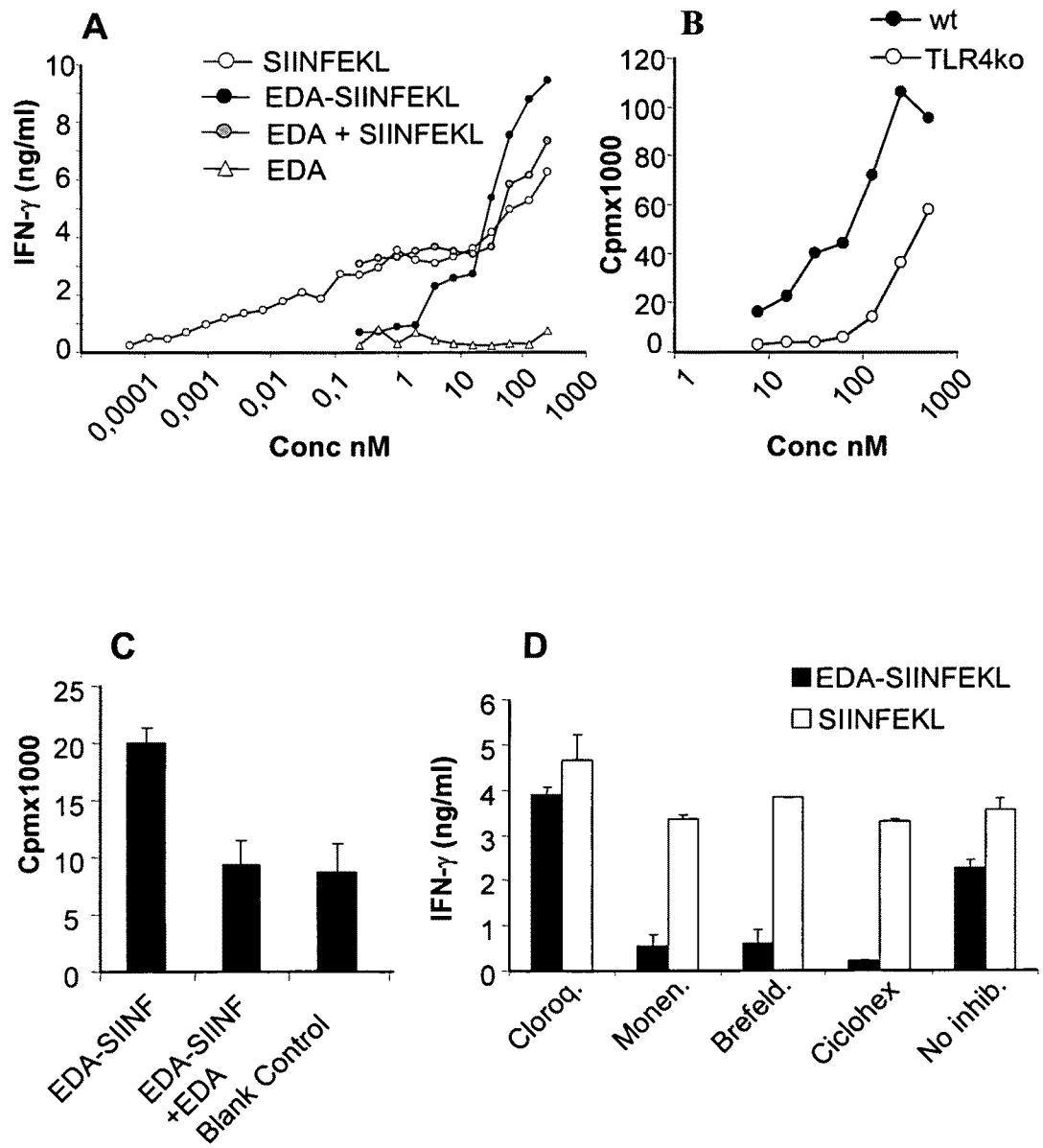
Figura 6

SEQUENCE LISTING

<160> NUMBER OF SEQ ID NOS: 23

<210> SEQ ID NO 1
<211> LENGTH: 348
<212> TYPE: DNA
<213> ORGANISM: Artificial Sequence
<220> FEATURE:
<223> OTHER INFORMATION: Synthetic Construct; Recombinant proteinaceous
      vector

<400> SEQUENCE: 1
atgaacattg atcgccctaa aggactggca ttcactgatg tggatgtcga ttccatcaaa       60
attgcttggg aaagcccaca ggggcaagtt tccaggtaca gggtgaccta ctcgagccct      120

```
gaggatggaa tccgggagct tttccctgca cctgatggtg aagacgacac tgcagagctg    180
cagggcctca ggccggggtc tgagtacaca gtcagtgtgg ttgccttgca cgatgatatg    240
gagagccagc ccctgattgg aatccagtcc acacagcttg agagtataat caactttgaa    300
aaactgactg aatgggcggc cgcactcgag caccaccacc accaccac                 348
```

<210> SEQ ID NO 2
<211> LENGTH: 116
<212> TYPE: PRT
<213> ORGANISM: Artificial Sequence
<220> FEATURE:
<223> OTHER INFORMATION: Synthetic Construct; Recombinant proteinaceous
      vector
<220> FEATURE:
<221> NAME/KEY: MISC_FEATURE
<222> LOCATION: (1)..(116)
<223> OTHER INFORMATION: Recombinant proteinaceous vector mEDA-SIINFEKL-
      6xHis (EDA-SIINFEKL), encoded by sequence SEQ. ID. NO.: 1
<220> FEATURE:
<221> NAME/KEY: MISC_FEATURE
<222> LOCATION: (2)..(91)
<223> OTHER INFORMATION: mouse EDA fibronectin domain (mEDA)
<220> FEATURE:
<221> NAME/KEY: MISC_FEATURE
<222> LOCATION: (92)..(105)
<223> OTHER INFORMATION: Peptide QLE-SIINFEKL-TEW
<220> FEATURE:
<221> NAME/KEY: MISC_FEATURE
<222> LOCATION: (111)..(116)
<223> OTHER INFORMATION: Histidine tail 6xHis

<400> SEQUENCE: 2

```
Met Asn Ile Asp Arg Pro Lys Gly Leu Ala Phe Thr Asp Val Asp Val
1               5                   10                  15

Asp Ser Ile Lys Ile Ala Trp Glu Ser Pro Gln Gly Gln Val Ser Arg
            20                  25                  30

Tyr Arg Val Thr Tyr Ser Ser Pro Glu Asp Gly Ile Arg Glu Leu Phe
        35                  40                  45

Pro Ala Pro Asp Gly Glu Asp Asp Thr Ala Glu Leu Gln Gly Leu Arg
    50                  55                  60

Pro Gly Ser Glu Tyr Thr Val Ser Val Val Ala Leu His Asp Asp Met
65                  70                  75                  80

Glu Ser Gln Pro Leu Ile Gly Ile Gln Ser Thr Gln Leu Glu Ser Ile
                85                  90                  95

Ile Asn Phe Glu Lys Leu Thr Glu Trp Ala Ala Ala Leu Glu His His
            100                 105                 110

His His His His
        115
```

<210> SEQ ID NO 3
<211> LENGTH: 255
<212> TYPE: DNA
<213> ORGANISM: Homo sapiens

<400> SEQUENCE: 3

```
aacattgatc gccctaaagg actggcattc actgatgtgg atgtcgattc catcaaaatt    60
gcttgggaaa gcccacaggg gcaagtttcc aggtacaggg tgacctactc gagccctgag   120
gatggaatcc atgagctatt ccctgcacct gatggtgaag aagacactgc agagctgcaa   180
ggcctcagac cgggttctga gtacacagtc agtgtggttg ccttgcacga tgatatggag   240
agccagcccc tgatt                                                    255
```

-continued

```
<210> SEQ ID NO 4
<211> LENGTH: 85
<212> TYPE: PRT
<213> ORGANISM: Homo sapiens

<400> SEQUENCE: 4

Asn Ile Asp Arg Pro Lys Gly Leu Ala Phe Thr Asp Val Asp Val
1               5                   10                  15

Ser Ile Lys Ile Ala Trp Glu Ser Pro Gln Gly Gln Val Ser Arg Tyr
            20                  25                  30

Arg Val Thr Tyr Ser Ser Pro Glu Asp Gly Ile His Glu Leu Phe Pro
        35                  40                  45

Ala Pro Asp Gly Glu Glu Asp Thr Ala Glu Leu Gln Gly Leu Arg Pro
    50                  55                  60

Gly Ser Glu Tyr Thr Val Ser Val Val Ala Leu His Asp Asp Met Glu
65                  70                  75                  80

Ser Gln Pro Leu Ile
                85

<210> SEQ ID NO 5
<211> LENGTH: 246
<212> TYPE: DNA
<213> ORGANISM: Artificial Sequence
<220> FEATURE:
<223> OTHER INFORMATION: Synthetic Construct; Recombinant proteinaceous
      vector

<400> SEQUENCE: 5
atgaacattg atcgccctaa aggactggca ttcactgatg tggatgtcga ttccatcaaa      60
attgcttggg aaagcccaca ggggcaagtt tccaggtaca gggcctcagg ccggggtctg    120
agaacacagt cagtgtggtt gccttgcacg atgatatgga gagccagccc ccagcttgag    180
agtataatca actttgaaaa actgactgaa tgggcggtcg cactcgagca ccaccaccac    240
caccac                                                               246

<210> SEQ ID NO 6
<211> LENGTH: 82
<212> TYPE: PRT
<213> ORGANISM: Artificial Sequence
<220> FEATURE:
<223> OTHER INFORMATION: Synthetic Construct; Recombinant proteinaceous
      vector
<220> FEATURE:
<221> NAME/KEY: misc_feature
<222> LOCATION: (1)..(82)
<223> OTHER INFORMATION: Recombinant proteinaceous vector mEDAalt-
      SIINFEKL-6xHis, encoded by sequence SEQ. ID. NO.: 5
<220> FEATURE:
<221> NAME/KEY: misc_feature
<222> LOCATION: (2)..(57)
<223> OTHER INFORMATION: Mouse alternative EDA domain of fibronectin
      (mEDAalt), generated by alternative splicing
<220> FEATURE:
<221> NAME/KEY: misc_feature
<222> LOCATION: (58)..(71)
<223> OTHER INFORMATION: Peptide QLE-SIINFEKL-TEW
<220> FEATURE:
<221> NAME/KEY: misc_feature
<222> LOCATION: (77)..(82)
<223> OTHER INFORMATION: Histidine tail
```

<400> SEQUENCE: 6

Met Asn Ile Asp Arg Pro Lys Gly Leu Ala Phe Thr Asp Val Asp Val
1               5                   10                  15

Asp Ser Ile Lys Ile Ala Trp Glu Ser Pro Gln Gly Gln Val Ser Arg
            20                  25                  30

Tyr Arg Ala Ser Gly Arg Gly Leu Arg Thr Gln Ser Val Trp Leu Pro
        35                  40                  45

Cys Thr Met Ile Trp Arg Ala Ser Pro Gln Leu Glu Ser Ile Ile Asn
50                  55                  60

Phe Glu Lys Leu Thr Glu Trp Ala Val Ala Leu Glu His His His His
65                  70                  75                  80

His His

<210> SEQ ID NO 7
<211> LENGTH: 168
<212> TYPE: DNA
<213> ORGANISM: Homo sapiens

<400> SEQUENCE: 7
aacattgatc gccctaaagg actggcattc actgatgtgg atgtcgattc catcaaaatt     60
gcttgggaaa gcccacaggg gcaagtttcc aggtacaggg cctcagaccg ggttctgagt    120
acacagtcag tgtggttgcc ttgcacgatg atatggagag ccagcccc                168

<210> SEQ ID NO 8
<211> LENGTH: 56
<212> TYPE: PRT
<213> ORGANISM: Homo sapiens

<400> SEQUENCE: 8

Asn Ile Asp Arg Pro Lys Gly Leu Ala Phe Thr Asp Val Asp Val Asp
1               5                   10                  15

Ser Ile Lys Ile Ala Trp Glu Ser Pro Gln Gly Gln Val Ser Arg Tyr
            20                  25                  30

Arg Ala Ser Asp Arg Val Leu Ser Thr Gln Ser Val Trp Leu Pro Cys
        35                  40                  45

Thr Met Ile Trp Arg Ala Ser Pro
50                  55

<210> SEQ ID NO 9
<211> LENGTH: 909
<212> TYPE: DNA
<213> ORGANISM: Artificial Sequence
<220> FEATURE:
<223> OTHER INFORMATION: Synthetic Construct; Recombinant proteinaceous
      vector

<400> SEQUENCE: 9
atgaacattg atcgccctaa aggactggca ttcactgatg tggatgtcga ttccatcaaa     60
attgcttggg aaagcccaca ggggcaagtt tccaggtaca gggtgaccta ctcgagccct    120
gaggatggaa tccgggagct ttttccctgca cctgatggtg aagacgacac tgcagagctg    180
cagggcctca ggccgggtc tgagtacaca gtcagtgtgg ttgccttgca cgatgatatg    240
gagagccagc ccctgattgg aatccagtcc acagcggccg cagccaccat ggcgcctatc    300
acggcctatt cccaacaaac gcggggcctg cttggctgta tcatcactag cctcacaggt    360
cgggacaaga accaggtcga tggggaggtt caggtgctct ccaccgcaac gcaatctttc    420
ctggcgacct gcgtcaatgg cgtgtgttgg accgtctacc atggtgccgg ctcgaagacc    480

-continued

```
ctggccggcc cgaagggtcc aatcacccaa atgtacacca atgtagacca ggacctcgtc   540
ggctggccgg cgccccccgg ggcgcgctcc atgacaccgt gcacctgcgg cagctcggac   600
ctttacttgg tcacgaggca tgccgatgtc attccggtgc gccggcgagg cgacagcagg   660
gggagtctac tctcccctag gcccgtctcc tacctgaagg gctcctcggg tggaccactg   720
ctttgccctt cggggcacgt tgtaggcatc ttccggctg ctgtgtgcac ccgggggtt    780 gcgaaggcgg tggacttcat acccgttgag tctatggaaa ctaccatgcg gtctccggtc   840
ttcacagaca actcatcccc tccggccgta ccgcaagcgg ccgcactcga gcaccaccac   900
caccaccac                                                           909
```

```
<210> SEQ ID NO 10
<211> LENGTH: 303
<212> TYPE: PRT
<213> ORGANISM: Artificial Sequence
<220> FEATURE:
<223> OTHER INFORMATION: Synthetic Construct; Recombinant proteinaceous
      vector
<220> FEATURE:
<221> NAME/KEY: MISC_FEATURE
<222> LOCATION: (1)..(303)
<223> OTHER INFORMATION: Recombinant proteinaceous vector mEDA-NS3-6xHis
      (EDA-NS3), encoded by sequence SEQ. ID. NO.: 9
<220> FEATURE:
<221> NAME/KEY: MISC_FEATURE
<222> LOCATION: (2)..(91)
<223> OTHER INFORMATION: Mouse EDA fibronectin domain (mEDA)
<220> FEATURE:
<221> NAME/KEY: MISC_FEATURE
<222> LOCATION: (97)..(292)
<223> OTHER INFORMATION: NS3 protein from hepatitis C virus
<220> FEATURE:
<221> NAME/KEY: MISC_FEATURE
<222> LOCATION: (298)..(303)
<223> OTHER INFORMATION: Histidine tail

<400> SEQUENCE: 10

Met Asn Ile Asp Arg Pro Lys Gly Leu Ala Phe Thr Asp Val Asp Val
1               5                   10                  15

Asp Ser Ile Lys Ile Ala Trp Glu Ser Pro Gln Gly Gln Val Ser Arg
            20                  25                  30

Tyr Arg Val Thr Tyr Ser Ser Pro Glu Asp Gly Ile Arg Glu Leu Phe
        35                  40                  45

Pro Ala Pro Asp Gly Glu Asp Asp Thr Ala Glu Leu Gln Gly Leu Arg
    50                  55                  60

Pro Gly Ser Glu Tyr Thr Val Ser Val Val Ala Leu His Asp Met
65                  70                  75                  80

Glu Ser Gln Pro Leu Ile Gly Ile Gln Ser Thr Ala Ala Ala Thr
                85                  90                  95

Met Ala Pro Ile Thr Ala Tyr Ser Gln Gln Thr Arg Gly Leu Leu Gly
            100                 105                 110

Cys Ile Ile Thr Ser Leu Thr Gly Arg Asp Lys Asn Gln Val Asp Gly
        115                 120                 125

Glu Val Gln Val Leu Ser Thr Ala Thr Gln Ser Phe Leu Ala Thr Cys
    130                 135                 140

Val Asn Gly Val Cys Trp Thr Val Tyr His Gly Ala Gly Ser Lys Thr
145                 150                 155                 160

Leu Ala Gly Pro Lys Gly Pro Ile Thr Gln Met Tyr Thr Asn Val Asp
                165                 170                 175

Gln Asp Leu Val Gly Trp Pro Ala Pro Gly Ala Arg Ser Met Thr
            180                 185                 190
```

```
Pro Cys Thr Cys Gly Ser Ser Asp Leu Tyr Leu Val Thr Arg His Ala
            195                 200                 205

Asp Val Ile Pro Val Arg Arg Gly Asp Ser Arg Gly Ser Leu Leu
    210                 215                 220

Ser Pro Arg Pro Val Ser Tyr Leu Lys Gly Ser Ser Gly Pro Leu
225                 230                 235                 240

Leu Cys Pro Ser Gly His Val Val Gly Ile Phe Arg Ala Ala Val Cys
                245                 250                 255

Thr Arg Gly Val Ala Lys Ala Val Asp Phe Ile Pro Val Glu Ser Met
            260                 265                 270

Glu Thr Thr Met Arg Ser Pro Val Phe Thr Asp Asn Ser Ser Pro Pro
        275                 280                 285

Ala Val Pro Gln Ala Ala Ala Leu Glu His His His His His His
    290                 295                 300
```

<210> SEQ ID NO 11
<211> LENGTH: 1473
<212> TYPE: DNA
<213> ORGANISM: Artificial Sequence
<220> FEATURE:
<223> OTHER INFORMATION: Synthetic Construct; Recombinant proteinaceous
      vector

<400> SEQUENCE: 11

```
atgaacattg atcgccctaa aggactggca ttcactgatg tggatgtcga ttccatcaaa     60
attgcttggg aaagcccaca ggggcaagtt tccaggtaca gggtgaccta ctcgagccct    120
gaggatggaa tccgggagct tttccctgca cctgatggtg aagacgacac tgcagagctg    180
cagggcctca ggccggggtc tgagtacaca gtcagtgtgg ttgccttgca cgatgatatg    240
gagagccagc ccctgattgg aatccagtcc acagcggccg caatgggctc catcggcgca    300
gcaagcatgg aatttttgttt tgatgtattc aaggagctca agtccacca tgccaatgag    360
aacatcttct actgccccat tgccatcatg tcagctctag ccatggtata cctgggtgca    420
aaagacagca ccaggacaca gataaataag gttgttcgct ttgataaact tccaggattc    480
ggagacagta ttgaagctca gtgtggcaca tctgtaaacg ttcactcttc acttagagac    540
atcctcaacc aaatcaccaa accaaatgat gtttattcgt tcagccttgc cagtagactt    600
tatgctgaag agagataccc aatcctgcca gaatacttgc agtgtgtgaa ggaactgtat    660
agaggaggct tggaacctat caactttcaa acagctgcag atcaagccag agagctcatc    720
aattcctggg tagaaagtca gacaaatgga attatcagaa atgtccttca gccaagctcc    780
gtggattctc aaactgcaat ggttctggtt aatgccattg tcttcaaagg actgtgggag    840
aaaacattta aggatgaaga cacacaagca atgcctttca gagtgactga gcaagaaagc    900
aaacctgtgc agatgatgta ccagattggt ttatttagag tggcatcaat ggcttctgag    960
aaaatgaaga tcctggagct tccatttgcc agtgggacaa tgagcatgtt ggtgctgttg   1020
cctgatgaag tctcaggcct tgagcagctt gagagtataa tcaactttga aaaactgact   1080
gaatggacca gttctaatgt tatggaagag aggaagatca agtgtactt acctcgcatg   1140
aagatggagg aaaaatacaa cctcacatct gtcttaatgg ctatgggcat tactgacgtg   1200
tttagctctt cagccaatct gtctggcatc tcctcagcag agagcctgaa gatatctcaa   1260
gctgtccatg cagcacatgc agaaatcaat gaagcaggca gagaggtggt agggtcagca   1320
gaggctggag tggatgctgc aagcgtctct gaagaattta gggctgacca tccattcctc   1380
```

```
ttctgtatca agcacatcgc aaccaacgcc gttctcttct tggcagatg tgtttcccct    1440 gcggccgcac tcgagcacca ccaccaccac cac                                1473
```

<210> SEQ ID NO 12
<211> LENGTH: 491
<212> TYPE: PRT
<213> ORGANISM: Artificial Sequence
<220> FEATURE:
<223> OTHER INFORMATION: Synthetic Construct; Recombinant proteinaceous
      vector
<220> FEATURE:
<221> NAME/KEY: MISC_FEATURE
<222> LOCATION: (1)..(491)
<223> OTHER INFORMATION: Recombinant proteinaceous vector mEDA-OVA-6xHis
      (EDA-OVA), encoded by sequence SEQ. ID. NO.: 11
<220> FEATURE:
<221> NAME/KEY: MISC_FEATURE
<222> LOCATION: (2)..(91)
<223> OTHER INFORMATION: Mouse EDA domain of fibronectin (mEDA)
<220> FEATURE:
<221> NAME/KEY: MISC_FEATURE
<222> LOCATION: (95)..(480)
<223> OTHER INFORMATION: OVA protein
<220> FEATURE:
<221> NAME/KEY: MISC_FEATURE
<222> LOCATION: (486)..(491)
<223> OTHER INFORMATION: Histidine tail

<400> SEQUENCE: 12

```
Met Asn Ile Asp Arg Pro Lys Gly Leu Ala Phe Thr Asp Val Asp Val
1               5                   10                  15

Asp Ser Ile Lys Ile Ala Trp Glu Ser Pro Gln Gly Gln Val Ser Arg
            20                  25                  30

Tyr Arg Val Thr Tyr Ser Ser Pro Glu Asp Gly Ile Arg Glu Leu Phe
        35                  40                  45

Pro Ala Pro Asp Gly Glu Asp Asp Thr Ala Glu Leu Gln Gly Leu Arg
    50                  55                  60

Pro Gly Ser Glu Tyr Thr Val Ser Val Val Ala Leu His Asp Asp Met
65                  70                  75                  80

Glu Ser Gln Pro Leu Ile Gly Ile Gln Ser Thr Ala Ala Ala Met Gly
                85                  90                  95

Ser Ile Gly Ala Ala Ser Met Glu Phe Cys Phe Asp Val Phe Lys Glu
            100                 105                 110

Leu Lys Val His His Ala Asn Glu Asn Ile Phe Tyr Cys Pro Ile Ala
        115                 120                 125

Ile Met Ser Ala Leu Ala Met Val Tyr Leu Gly Ala Lys Asp Ser Thr
    130                 135                 140

Arg Thr Gln Ile Asn Lys Val Val Arg Phe Asp Lys Leu Pro Gly Phe
145                 150                 155                 160

Gly Asp Ser Ile Glu Ala Gln Cys Gly Thr Ser Val Asn Val His Ser
                165                 170                 175

Ser Leu Arg Asp Ile Leu Asn Gln Ile Thr Lys Pro Asn Asp Val Tyr
            180                 185                 190

Ser Phe Ser Leu Ala Ser Arg Leu Tyr Ala Glu Glu Arg Tyr Pro Ile
        195                 200                 205

Leu Pro Glu Tyr Leu Gln Cys Val Lys Glu Leu Tyr Arg Gly Gly Leu
    210                 215                 220

Glu Pro Ile Asn Phe Gln Thr Ala Ala Asp Gln Ala Arg Glu Leu Ile
225                 230                 235                 240

Asn Ser Trp Val Glu Ser Gln Thr Asn Gly Ile Ile Arg Asn Val Leu
                245                 250                 255
```

```
Gln Pro Ser Ser Val Asp Ser Gln Thr Ala Met Val Leu Val Asn Ala
            260                 265                 270
Ile Val Phe Lys Gly Leu Trp Glu Lys Thr Phe Lys Asp Glu Asp Thr
        275                 280                 285
Gln Ala Met Pro Phe Arg Val Thr Glu Gln Glu Ser Lys Pro Val Gln
    290                 295                 300
Met Met Tyr Gln Ile Gly Leu Phe Arg Val Ala Ser Met Ala Ser Glu
305                 310                 315                 320
Lys Met Lys Ile Leu Glu Leu Pro Phe Ala Ser Gly Thr Met Ser Met
                325                 330                 335
Leu Val Leu Leu Pro Asp Glu Val Ser Gly Leu Glu Gln Leu Glu Ser
            340                 345                 350
Ile Ile Asn Phe Glu Lys Leu Thr Glu Trp Thr Ser Ser Asn Val Met
        355                 360                 365
Glu Glu Arg Lys Ile Lys Val Tyr Leu Pro Arg Met Lys Met Glu Glu
    370                 375                 380
Lys Tyr Asn Leu Thr Ser Val Leu Met Ala Met Gly Ile Thr Asp Val
385                 390                 395                 400
Phe Ser Ser Ser Ala Asn Leu Ser Gly Ile Ser Ser Ala Glu Ser Leu
                405                 410                 415
Lys Ile Ser Gln Ala Val His Ala Ala His Ala Glu Ile Asn Glu Ala
            420                 425                 430
Gly Arg Glu Val Val Gly Ser Ala Glu Ala Gly Val Asp Ala Ala Ser
        435                 440                 445
Val Ser Glu Glu Phe Arg Ala Asp His Pro Phe Leu Phe Cys Ile Lys
    450                 455                 460
His Ile Ala Thr Asn Ala Val Leu Phe Phe Gly Arg Cys Val Ser Pro
465                 470                 475                 480
Ala Ala Ala Leu Glu His His His His His His
                485                 490

<210> SEQ ID NO 13
<211> LENGTH: 30
<212> TYPE: DNA
<213> ORGANISM: Artificial Sequence
<220> FEATURE:
<223> OTHER INFORMATION: Synthetic Construct; Synthetic oligonucleotide

<400> SEQUENCE: 13
ccatatgaac attgatcgcc ctaaaggact                              30

<210> SEQ ID NO 14
<211> LENGTH: 75
<212> TYPE: DNA
<213> ORGANISM: Artificial Sequence
<220> FEATURE:
<223> OTHER INFORMATION: Synthetic Construct; Synthetic oligonucleotide

<400> SEQUENCE: 14
agcggccgcc cattcagtca gttttcaaa gttgattata ctctcaagct gtgtggactg    60
gattccaatc agggg                                              75

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct; Synthetic oligonucleotide
```

```
<400> SEQUENCE: 15
agcggccgct gtggactgga ttccaatcag ggg                                33

<210> SEQ ID NO 16
<211> LENGTH: 27
<212> TYPE: DNA
<213> ORGANISM: Artificial Sequence
<220> FEATURE:
<223> OTHER INFORMATION: Synthetic Construct; Synthetic oligonucleotide

<400> SEQUENCE: 16
gcggccgcaa tgggctccat cggcgca                                      27

<210> SEQ ID NO 17
<211> LENGTH: 23
<212> TYPE: DNA
<213> ORGANISM: Artificial Sequence
<220> FEATURE:
<223> OTHER INFORMATION: Synthetic Construct; Synthetic oligonucleotide

<400> SEQUENCE: 17
gcggccgcag gggaaacaca tct                                          23

<210> SEQ ID NO 18
<211> LENGTH: 39
<212> TYPE: DNA
<213> ORGANISM: Artificial Sequence
<220> FEATURE:
<223> OTHER INFORMATION: Synthetic Construct; Synthetic oligonucleotide

<400> SEQUENCE: 18
agcggccgca gccaccatgg cgcctatcac ggcctattc                         39

<210> SEQ ID NO 19
<211> LENGTH: 36
<212> TYPE: DNA
<213> ORGANISM: Artificial Sequence
<220> FEATURE:
<223> OTHER INFORMATION: Synthetic Construct; Synthetic oligonucleotide

<400> SEQUENCE: 19
agcggccgct tgcggtacgg ccggaggggga tgagtt                           36

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct; Synthetic peptide

<400> SEQUENCE: 20

Cys Val Asn Gly Val Cys Trp Thr Val
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct; Synthetic peptide

<400> SEQUENCE: 21

Cys Leu Asn Gly Val Cys Trp Thr Val
1               5
```

```
<210> SEQ ID NO 22
<211> LENGTH: 9
<212> TYPE: PRT
<213> ORGANISM: Artificial Sequence
<220> FEATURE:
<223> OTHER INFORMATION: Synthetic Construct; Synthetic peptide

<400> SEQUENCE: 22

Leu Leu Cys Pro Ala Gly His Ala Val
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct; Synthetic peptide

<400> SEQUENCE: 23

Gly Leu Leu Gly Cys Ile Ile Thr Ser
1               5
```

AGENTS AND METHODS BASED ON THE USE OF THE EDA DOMAIN OF FIBRONECTIN

TECHNICAL FIELD OF THE INVENTION

The present invention relates to a proteinaceous vector for molecular transport to cells that express TLR4 receptor (Toll-like receptor 4), the preparation of said proteinaceous vector and its applications, with a particular incidence on the preparation and use of pharmaceutical compositions, particularly immunotherapeutic compositions, for the treatment and prevention of infectious and tumoral disease.

DESCRIPTION OF THE PRIOR ART

Pathogens and cancer remain the leading causes of death worldwide. The development of vaccines to prevent diseases for which no vaccine currently exists, such as AIDS or malaria, or to treat chronic infections or cancers, as well as the improvement of efficacy and safety of existing vaccines, remains a high priority. In most cases, the development of such vaccines requires strategies capable of specifically stimulating CDB+cytotoxic T lymphocytes (CTLs).

CTLs are activated by the presentation to T-cell receptors (TCRs) of short peptides associated with MHC class I molecules. These peptide-MHC class I complexes are present on the surface of antigen-presenting cells (APCs), which are also capable of providing co-stimulatory signals required for optimal CTL activation.

Dendritic cells (DC) are the most potent APCs, with a unique capacity to interact with naive T lymphocytes and initiate primary immune responses, activating helper CD4+ and cytotoxic CD8+ T lymphocytes. Antigen presentation and T cell stimulation by DC is reviewed by Guermonprez et al. ("Antigen presentation and T cell stimulation by DC". *Annu. Rev. Immunol.* 2002, 20:621-627), which is here included by reference.

In the absence of ongoing inflammatory and immune responses, dendritic cells patrol through the blood, peripheral tissues, lymph, and secondary lymphoid organs. In peripheral tissues, dendritic cells take up self and non-self antigens. Internalized antigens are then processed into proteolytic peptides, and these peptides are loaded onto MHC class I and II molecules (for CD8+ or CD4+ T lymphocyte activation, respectively). This process of antigen uptake, degradation, and loading is called antigen presentation. However, in the absence of stimulation, peripheral dendritic cells present antigens quite inefficiently. Exogenous signal(s) from pathogens or endogenous signal(s) induce(s) dendritic cells to enter a developmental program, called maturation, which transforms dendritic cells into APCs and T lymphocyte activators. Bacterial and viral products, as well as inflammatory cytokines and other self-molecules, induce dendritic cell maturation through direct interaction with innate dendritic cell surface receptors. T lymphocytes, through CD40-dependent and -independent pathways, and endothelial cells contribute to the final maturation of dendritic cells through direct cell-to-cell contact and the secretion of cytokines. Soon after encountering a danger signal, the efficiency of antigen uptake, intracellular transport and degradation, and the intracellular traffic of MHC molecules are modified. Peptide loading as well as the half-life and delivery to the cell surface of MHC molecules is increased. The surface expression of T cell costimulatory molecules also rises. Thus, dendritic cells become the most potent APCs, and the only ones capable of activating naive T lymphocytes and of initiating adaptive immune responses. Concomitant with the modifications of their antigen presenting abilities, maturation also induces massive migration of dendritic cells out of peripheral tissues. Modifications in the expression of chemokine receptors and adhesion molecules, as well as profound changes of the cytoskeleton organization, contribute to the migration of dendritic cells, through the lymph, toward secondary lymphoid organs.

Induction of Dendritic Cell Maturation.

Dendritic cells respond to two types of signals: direct recognition of pathogens (through specific pattern-recognition receptors) and indirect sensing of infection (through inflammatory cytokines, internal cellular compounds, and ongoing specific immune responses). In response to these signals, dendritic cells are activated and enter the maturation program, which transforms dendritic cells into efficient T cell stimulators. At least five types of surface receptors have been reported to trigger dendritic cell maturation: (i) Toll-like receptors (TLR), (ii) cytokine receptors, (iii) TNF-receptor (TNF-R) family molecules, (iv) FcR, and (v) sensors for cell death. Some of the most efficient maturation stimuli are mediated by TLR (TLR1-9) interaction with their respective ligands. Kaisho and Akira reviewed knowledge about Toll-like receptors ("Toll-like receptors as adjuvant receptors". Biochimica et *Biophysica Acta,* 2002, 1589: 1-13). TLR are expressed on macrophages and dendritic cells as well as on other cells such as B lymphocytes. Ligands for several of the TLRs have also been identified. Most of these ligands are derived from pathogens, but not found in the host, suggesting that TLR are critical for sensing invading microorganisms. Ligand recognition by TLR provokes rapid activation of innate immunity by inducing production of proinflamatory cytokines and upregulation of costimulatory molecules. Activated innate immunity subsequently leads to effective adaptive immunity. Regarding TLR4, molecular patterns specifically recognized are LPS (Gram-bacteria), lipoteichoic acids (Gram+ bacteria), taxol, F protein (Respiratory Syncytial Virus), heat shock protein 60, and Fibronectin EDA domain.

Therefore, a candidate vaccine capable of inducing optimal T cell responses must fulfill several conditions. First, it has to target APC to deliver the antigen-derived T cell epitopes to MHC class I and/or II molecules. Thus, targeting DC could represent the main objective in designing new delivery systems for vaccine development. Furthermore, the vector has to deliver appropriate signals to DC to induce their activation. Antigen delivery to DC without a maturation signal could induce tolerance rather than activation of T helper and cytotoxic cells. In addition, its efficiency must not be affected by pre-existing immunity against the vector itself.

A first approach to deliver antigenic peptides to MHC class I and/or II molecules is based on synthetic peptide vaccines, containing selected epitopes capable of binding directly to these molecules on the surface of APC. In some cases these peptides have led to tumor protection or virus clearance in murine models, whereas in others they have led to tolerance induction. Human trials conducted with different types of peptides gave rise to modest clinical responses to cancer.

A large number of different strategies are currently under development. Basically, they can be divided into two categories. The first type is based on the synthesis of antigen by the APC or its active delivery into the cytoplasm of these cells and exploit the 'classical' MHC I antigen processing pathway. The second type takes advantage of the capacity of cross-presentation of APC and is based on free or cell-associated exogenous antigens. Delivery of antigen into the cytoplasm of APC has been performed by means of bacterial toxins (Morón et al. "New tools for antigen delivery to the MHC class I pathway". TRENDS in Immunology, 2004; 25: 92-97). As an example, EP1188446A1 relates to a proteinaceous vector based on *Bordetella pertussis* adenylate cyclase toxin, for molecule delivery to CD11b expressing cells.

The present invention relates to fibronectin Extra Domain A (EDA), a possible natural ligand for TLR4, as a theoretical means for antigen delivery to TLR4 expressing cells that could induce appropriate selection and maturation of APC, and finally lead to an effective specific CTL response. Fibronectin molecules are the products of a single gene, and the resulting protein can exist in multiple forms that arise from alternative splicing of a single pre-mRNA (Pankov R and Kenneth M Y, "Fibronectin at a glance". *Journal of Cell Science*, 2002; 115:3861-3863). A major type of splicing occurs within the central set of type III repeats. Exon usage or skipping leads to inclusion or exclusion of either of two type III repeats: extra domain B (also termed EDB, EIIIB or EDII), and extra domain A (also termed EDA, EIIIA or EDI). Cellular fibronectins, which contain alternatively spliced EDA and EDB, are produced in response to tissue injury. Among other biological functions, EDA has been shown to induce proteoglycan release, and expression of metalloproteinases (MMP 1, 3, and 9) and of pro-inflammatory cytokines (for review see Saito S et al. "The Fibronectin Extradomain A activates matrix metalloproteinase gene expression by an interleukin-1-dependent mechanism", *J. Biol. Chem.* 1999; 161:3071-3076). It has also been described that EDA is capable of activating TLR4, thus inducing LPS-like responses (Okamura Y et al., "The extra domain A of fibronectin activates Toll-like receptor 4", *J. Biol. Chem.* 2001; 276:10229-10233).

As indicated previously, the development of strategies for the strengthening the immune response to an antigen, opens the door to the development of vaccines for the treatment of cancer or infectious diseases. Specifically, in hepatitis C virus infection it has been described that the immune response plays an essential role in the clearance of infection, therefore the use of immunostrengthening strategies constitute an alternative for the treatment and prevention of this infection.

Hepatitis C virus (HCV) is a single strand RNA virus that belongs to the Flaviviridae family (Miller R H. and Purcell R H. 1990. PNAS. 87:2057). This virus has been recognised as one of the main causal agents of chronic hepatitis and liver diseases and it is estimated that it affects 170 million people worldwide (World-Health-Organisation. Hepatitis C. Wkly Epidemiol Rec 1997; 72:65). One of the main features of HCV infection is its high tendency towards chronicity (70% of infections) and the development of liver cirrhosis (20%) with a high risk of development of hepatocarcinomas (Dienstag et al. Gastroenterology 1983; 85:439). Treatment with IFN-α is the most common therapy in HCV infections, but it is only efficient in 20-30% of treated patients (Camps et al. J Hepatol 1993; 17:390). The combination of IFN-α and ribavirin has bettered these results (30-40% of patients clear the virus in a sustained manner), but there still remains a high percentage of patients resistant to therapy (Poynard et al. Lancet 1998; 352:1426). Thus, the development of new therapeutic strategies for the treatment of chronic hepatitis C is of vital importance.

HCV genome is of 9.6 kilobases, it contains highly conserved non-coding regions at the 5' and 3' ends flanking an ample reading frame that encodes 3 structural proteins (core, E1 and E2) and at least 6 non-structural proteins (NS2, NS3, NS4a, NS5a and NS5b) (Major, ME and Feinstone SM. (1997) Hepatology 25, 1527).

Viral clearance after an acute infection by HCV or after treatment with IFN-α is associated to the presence of a strong cellular CD4 and CD8 immune response to viral proteins. Particularly, CD4 response to the HCV non-structural NS3 protein has been associated to viral clearance after acute infection, whereas the absence of this T cell response involves viral persistance and the establishment of a chronic infection (Diepolder et al. Lancet 1995; 346:1006, Pape et al J Viral Hepat 1999; 6 Suppl 1:26-40). Also, various studies have identified various cytotoxic epitopes within NS3 protein in patients infected by HCV. These data suggest that NS3 protein could be a good target for the induction of anti-HCV cellular response.

DETAILED DESCRIPTION OF THE INVENTION

In one aspect, the present invention relates to the use of a polypeptide comprising the amino acid sequence corresponding to:
  fibronectin EDA domain (EDA), or
  a fragment of said EDA domain that is capable of binding TLR4, or
  a variant of said EDA domain or fragment which is capable of binding TLR4 and has more than 70% homology with any EDA domain natural forms or fragments,
in the manufacture of an immune cell response to antigen stimulatory agent.

In the present invention, this agent includes both EDA domain of fibronectin and the antigen to which it is desired to generate the immune response, these components being present as separate entities or bound covalently.

In a concrete realization of the invention, said variant of the EDA domain or fragment capable of binding TLR4 cited in element c), is characterised in that its amino acid sequence results from the substitution, addition or deletion of one or more amino acids in a polypeptide defined in elements a) and b).

In a preferable realization of the invention, said fragment capable of binding element c), is characterised in that it has an over 85% degree of homology with any natural form of EDA domain or its corresponding fragment, and in a more preferable realization, it has an over 95% degree of homology with said natural form of fibronectin EDA domain or its corresponding fragment.

According to the invention, in a particular realization the amino acid sequence of fibronectin EDA domain is that of any natural form of EDA that is capable of binding TLR4. This EDA domain may be selected among the natural forms of the domain in any animal species, particularly mammals, i.e. rodents (mice, rats, etc), or primates (particularly humans).

In another specific realization the immunostimulatory agents comprises a partial amino acid sequence of an EDA domain that is characterised in that it is capable of binding TLR4.

In yet another particular realization of the invention, EDA domain is a modified variant of any of said EDA domain natural forms or fragments, and is also characterized in that it retains the property of binding to TLR4. In a particular embodiment such a variant EDA domain has more than 70% homology with any of the EDA domain natural forms. An appropriate modified variant can be selected by first comparing the sequence of a fibronectin EDA domain natural form, or fragment of the same, with other candidate polypeptidic sequences. Any alignment algorithm (for example FASTA, Lipman D J, Pearson W R. Rapid and sensitive protein similarity searches, Science. 1985 Mar. 22; 227(4693):1435-41), or computer software (i.e. Jellifish from Labvelocity Inc., or Blast software from NCBI) can be used for homology analysis. Subsequently, the candidate polypeptidic sequences having more than 70% homology are tested for their TLR4 binding capacity. TLR4 binding properties can be evaluated by means of any conventional binding assay, for example by using flow cytometry as described in The Current Protocols in Immunology and in The current protocols in Protein Science published by John Wiley & Sons (Edited by: John E. Coligan, Ada M. Kruisbeek, David H. Margulies, Ethan M. Shevach, Warren Strober) (periodically updated. Updated up to May 1, 2005).

In one embodiment of the invention the EDA domain comprises a sequence selected from:
a) the complete amino acid sequence of mouse EDA domain (Entrez Protein: NM_010233, amino acids 1721 to 1810; SEQ. ID. NO: 2, amino acids 2-91);
b) the complete amino acid sequence of human EDA domain (Entrez Protein NM_002026, amino acids 1631 to 1716; SEQ. ID. NO: 4); and
c) a fragment of sequences a) and b) capable of binding to TLR4 expressing cells.

In another particular realization, said EDA domain comprises a sequence selected from:
a) amino acids 2-57 of SEQ. ID. NO: 6, which corresponds to an alternatively spliced form of mouse fibronectin EDA domain;
b) SEQ. ID. NO: 8, which is an alternatively spliced form of human EDA domain; and
c) a fragment of sequences a) and b) capable of binding to TLR4 expressing cells.

In some embodiments, the immunostimulatory agent may further include one or more molecules of interest. When present in the immunostimulatory agent, the molecule of interest may be administered in an amount that, in combination with the other components of the agent, is effective to generate an immune response against the molecule.

In a preferred realization, EDA domain (or fragment or variant thereof) and the molecule of interest are linked together in the same hybrid molecule or proteinaceous vector.

In another aspect, the present invention relates to a proteinaceous vector as described above wherein said molecule of interest is selected from the group consisting of polypeptides, lipopeptides, oligosacharides, polysacharides, nucleic acids, lipids, and chemicals.

In a particular realization of the proteinaceous vector, said molecule of interest is an antigen or an epitope. In one embodiment of the invention the antigen coupled to the vector is a viral antigen, a bacterial antigen, a fungus antigen, or a parasitic antigen. In a concrete realization said viral antigen is a viral antigen from hepatitis C virus, and in a preferred realization said hepatitis C virus antigen id NS3 protein or an antigenic fragment of the same. NS3 protein refers to the hepatitis C virus non-structural NS3 protein, a 67 kDa protein that includes two domains, a serin-protease that comprises the 189 amino acids from the N-terminal end, and a helicase-nucleoside triphosphatase that comprises the 442 amino acids from the C-terminal end. The NS3 protein sequence included in the proteinaceous vector of the invention can correspond to any strain or isolate of human hepatitis C virus.

In another embodiment said antigen is a tumoral antigen or a tumoral antigenic determinant. As used herein, "epitope" refers to a peptide sequence that binds to MHC class I or class II molecules and can be recognized by the T cell receptor molecule of CD8+ or CD4+ T cells respectively, and induce an immune response.

In a specific realization said molecule of interest is the antigenic cytotoxic T determinant from ovalbumin (OVA 257-264) or SIINFEKL (SEQ. ID. NO: 2, amino acids 95-102, which has been flanked with 3 additional amino acids on the C-terminus and the N-terminus of the epitope, QLE-SIINFEKL-TEW).

The antigen may be any material capable of producing a Th immune response, a CD8+ T lymphocyte response, a NK cell response, a γ/δ T lymphocyte response, or an antibody response. Without being limited to them, appropriate antigens include peptides, polypeptides, lipids, glycolipids, polysaccharides, carbohydrates, polynucleotides, prions, bacteria, virus or live or inactivated fungi; and antigens derived from bacteria, virus, fungi, protozoans, tumours or microorganisms, toxins or toxoids.

In another particular realization of the proteinaceous vector said molecule of interest is an allergen.

This way, EDA domain acts also as a vector for antigen delivery to TLR4 expressing cells.

In another particularly interesting realization of the invention, said molecule of interest is a chemical or a drug chemically or genetically coupled to the proteinaceous vector. This way said proteinaceous vector is useful for specific drug targeting to TLR4 expressing cells.

In a particular realization the proteinaceous vector is also characterized in that it also comprises a Tag sequence, for example an N-terminal histidine-tail. This will simplify the purification process when the proteinaceous vector is manufactured by means of genetic engineering methods. As an example, sequences SEQ. ID. NO: 2 and SEQ. ID. NO: 6 represent specific realizations of the proteinaceous vector of the invention. In a concrete non limiting realization of the present invention, the proteinaceous vector comprises sequence SEQ ID NO: 10, which comprises a fragment of NS3 protein.

The EDA domain incorporated in the proteinaceous vector is characterized in that it binds to TLR4 and furthermore facilitates the translocation of the molecule of interest to the cytosol of TLR4 expressing cells.

The invention also refers to the use of the proteinaceous vector to target and translocate a molecule of interest to TLR4 expressing cells. In a particular realization, TLR4 expressing cells are any kind of antigen presenting cells (APC). In a preferred embodiment such APC are dendritic cells.

In a particular realization of the invention, the proteinaceous vector is characterized in that it facilitates the translocation of the antigen or epitope of interest, further favoring the processing, and loading on MHC molecules for antigen presentation to T lymphocytes.

In another realization, the proteinaceous vector is characterized in that it is capable of stimulating the maturation of the targeted APC, thus increasing expression of MHC molecules and of co-stimulatory signals. In a particular advantageous embodiment, the proteinaceous vector is characterized in that it is capable of simultaneously inducing antigen presentation and promoting APC maturation, thus inducing an effective antigen-specific immune response. In a more preferred embodiment this antigen-specific immune response is a CTL response.

The proteinaceous vector of the invention can be obtained by recombinant DNA technology. Thus, in another aspect, the invention relates to a modified nucleic acid encoding a proteinaceous vector of the invention. This nucleic acid can easily be deduced from the amino acid sequence of the proteinaceous vector.

This modified nucleic acid can be contained within a DNA construct. Thus, the invention provides a DNA construct comprising a nucleic acid that encodes the proteinaceous vector of the invention. This DNA construct can incorporate a control sequence operatively linked to the nucleic acid encoding the proteinaceous vector of the invention. "Operatively linked" when referring to nucleic acids means that the nucleic acids are placed in a functional relationship with another nucleic acid sequence. The "control sequences" are expression signals recognized by a specific host cell, which regulate functions such as transcription and translation of particular encoding sequences (examples of control sequences are promoters, enhancers, transcription terminators, ribosome binding sites, signal peptides for protein secretion or for other subcellular locations). Linking of desired sequences is accomplished by ligation at convenient restriction sites. If such sites do not exist, synthetic oligonucleotide adaptors or linkers are used in accordance with conventional methods. An advantage in this sense is represented by the fact that this DNA construct also comprises a marker or gene that encodes a motif or phenotype that allows selection of the transformed host cell by means of the DNA construct. The modified nucleic acid and DNA construct afforded by this invention can be obtained by means of well known conventional methods which are summarized in many laboratory handbooks (for example, "Molecular Cloning: a Laboratory manual." Joseph Sambrook, David W. Russel Eds. 2001, $3^{rd}$ ed. Cold Spring Harbor, N.Y.).

In a particular realization the modified nucleic acid or DNA construct provided by the invention comprises SEQ. ID. NO: 1, SEQ ID. NO: 5, SEQ ID NO: 9 (EDA-NS3) or SEQ ID NO: 11 (EDA-OVA).

The modified nucleic acid or DNA construct provided by this invention can be inserted in an appropriate vector. Thus, in another aspect, the invention relates to a vector, such as an expression vector, that comprises the mentioned modified nucleic acid or DNA construct. The choice of vector will depend on the host cell into which it is to be inserted. As an example, the vector into which the nucleic acid is inserted can be a plasmid or virus which, upon insertion into the cell, may or may not integrate in the cell genome. The vector can be obtained by conventional methods (Sambrook et al., 2001, cited supra).

In another aspect, the invention relates to a host cell, such as a transformed host cell, that comprises a modified nucleic acid or DNA construct provided by this invention. According to the invention, the expression host cell is a prokaryote, i.e. *Escherichia coli*, or an eukaryotic host, i.e. yeast (for example *Saccharomyces cerevisiae, Pichia Pastoris*), insect cells, or mammalian cells.

In another particular realization of the invention, the expression vector comprising the modified nucleic acid or DNA construct that encodes the proteinaceous vector of the invention, is intended for in vivo gene transfer or therapy. In a more particular embodiment, said expression vector is a viral vector. Appropriate viral vectors to this effect include: adenovirus, adenoassociated, retrovirus, lentivirus, alphavirus, herpesvirus, coronavirus derived vectors, etc.

In another aspect, the invention relates to a method for producing a proteinaceous vector of the invention, comprising culturing a host cell containing a modified nucleic acid or DNA construct of the invention, under conditions allowing expression of the proteinaceous vector. The conditions for optimizing culture of the host cell will depend on the type of host cell employed. If desired, the procedure for producing the proteinaceous vector of the invention includes isolation and purification of the same.

Alternatively, the proteinaceous vector of the invention can be obtained by other conventional methods. Such methods include, for example, solid phase chemical synthesis; purification with high performance liquid chromatography (HPLC); and, if preferred, analysis by conventional techniques such as sequencing or mass spectrometry, amino acid analysis, magnetic resonance techniques, etc.

In another realization, the proteinaceous vector of the invention can be obtained by covalent linkage of the polypeptide with the amino acid sequence corresponding to fibronectin EDA domain (EDA), or a fragment of said EDA domain capable of binding TLR4, or a variant of said EDA domain), with the molecule of interest (eg.: polypeptides, lipopeptides, oligosaccharides, polysaccharides, nucleic acids, lipids, or other chemicals). This can be performed by using conventional methods summarized in laboratory handbooks, for example, "The current protocols in protein chemistry", published by John Wiley & Sons (periodically updated. Updated up to May 1, 2005), or "Immobilized affinity ligand Techniques", G T Hermanson, A K Mallia and P K Smith, Academic Press, Inc. San Diego, Calif., 1992.

Subsequently, according to the invention the proteinaceous vector, or modified nucleic acid and DNA constructs encoding the same, or the expression vectors and expression host cells incorporating said nucleic acids or DNA constructs, can be used in the preparation of a pharmaceutical composition.

In another embodiment, the present invention refers to the use of the polypeptide with the amino acid sequence corresponding to fibronectin EDA domain (EDA), or a fragment or variant of the same, as previously described, in the preparation of a immunostimulatory agent, characterized in that said agent is a pharmaceutical composition.

In certain embodiments, the pharmaceutical composition of the invention may be used to stimulate the maturation of antigen presenting cells, or to induce an effective immune response specific for the molecule of interest. In a particular embodiment, said pharmaceutical composition may be used to induce a Th1 immune response in a subject to which the immunostimulatory composition is administered. As used herein, "inducing a Th1 immune response" can include instances in which the immunostimulatory composition induces a mixed Th1/Th2 response. In other cases, however, the immunostimulatory composition can induce a Th1 immune response with little or substantially no induction of a Th2 immune response. In a particular realization, said pharmaceutical composition may be used to induce a CTL response.

In some embodiments, the immunostimulatory composition may be used as an immunostimulatory adjuvant, e.g., combined with one or more antigens, either with or without additional adjuvants. Thus, in some cases, the immunostimulatory composition may form a vaccine. In other cases, the immunostimulatory composition may serve as an adjuvant that may be used in connection with a vaccine.

The immunostimulatory composition that includes the polypeptide comprising fibronectin EDA domain (or fragment or variant thereof) can enhance the expansion of activated CD8+ T lymphocytes, the generation of memory CD8+ T lymphocytes, or both. Thus, the immunostimulatory composition of the invention can enhance antigen-specific cell-mediated immunity in a subject that receives the immunostimulatory composition.

In a particular realization the immunostimulatory composition comprising fibronectin EDA domain (or fragment or variant thereof) is useful for the treatment and prophylaxis of an infectious disease, a tumoral disease, or an allergic disease. In a concrete embodiment of the present invention, said composition is used for the treatment and prophylaxis of hepatitis C.

The immunostimulatory composition comprising fibronectin EDA domain (or fragment or variant thereof) can contain additionally carriers, excipients, and other known pharmaceutically acceptable ingredients.

The immunostimulatory composition of the invention can be administered to animals, e.g., mammals (human or non-human), fowl, and the like, according to conventional methods well known to those skilled in the art (e.g., orally, subcutaneously, nasally, topically).

The invention also provides a therapeutic and/or prophylactic method that includes administering an immunostimulatory composition comprising fibronectin EDA domain (or fragment or variant thereof) to a subject.

Suitable routes of administration include transdermal or transmucosal absorption, injection (e.g., subcutaneous, intraperitoneal, intramuscular, intravenous, etc.), ingestion, inhalation, and the like.

In another further aspect, the invention relates to a pharmaceutical composition that includes at least one acceptable pharmaceutical carrier and an effective amount of the proteinaceous vector in at least one of its expression forms or embodiments:
a) the proteinaceous vector in polypeptidic form;
b) a modified nucleic acid that encodes said proteinaceous vector;
c) an expression vector comprising said modified nucleic acid; or
d) expression host cells also comprising said modified nucleic acid.

In another particular realization, the pharmaceutical composition is characterized in that it comprises an effective amount of dendritic cells, wherein said dendritic cells have been incubated in vitro with the proteinaceous vector in at least one of its expression forms or embodiments. In a more particular embodiment said pharmaceutical composition is a vaccine or immunotherapeutic composition.

Moreover, some additional uses of the proteinaceous vector are hereby provided. In one embodiment of the invention, the proteinaceous vector in any of it's expression forms is used for the preparation of a pharmaceutical composition effective for inducing dendritic cell maturation in vitro or in vivo.

In another embodiment, said proteinaceous vector is used for the preparation of a pharmaceutical composition for inducing a specific immune response specific against the molecule of interest (antigen or epitope) coupled to the proteinaceous vector. This immune response is a humoral immune response (antibody production against the molecule of interest), a T helper response, or a cytotoxic T cell response. In a preferred embodiment said immune response is a CTL response.

In a more particular realization, the invention relates to the use of the proteinaceous vector in the preparation of a pharmaceutical composition for the treatment and prophylaxis of an infectious disease. Said infectious disease may be a bacterial, viral, fungi or parasitic infectious disease.

In another particular realization, the invention relates to the use of the proteinaceous vector of the invention in the preparation of a pharmaceutical composition useful for the treatment and prophylaxis of a tumoral disease.

In yet another particular realization, the invention relates to the use of the proteinaceous vector in the preparation of a pharmaceutical composition useful for the treatment and prophylaxis of an allergic disease. A number of allergic diseases are related to the activation of a Th2 immune response. Thus, a deviation, or a switch from Th2 to a Th1 response by using the proteinaceous vector carrying a particular allergen, might have a protective or therapeutic effect on the allergic disease.

According to a particular embodiment of the invention, the proposed pharmaceutical composition is used for administration to an animal or human host. Any suitable administration route may be used. In a particular realization, the pharmaceutical composition is administered by a parenteral route (i.e. intravenous, subcutaneous, intramuscular), a transdermic route, or a mucosal route.

BRIEF DESCRIPTION OF THE DRAWINGS

FIG. 6: EDA-SIINFEKL is efficiently presented by dendritic cells to T cells specific for SIINFEKL epitope. We characterized the ability of EDA-SIINFEKL to be captured by APC for presentation of the processed CTL epitope SIINFEKL to T cells from OT-1 transgenic mice, specific for this epitope. (A) IFN-γ production by non-adherent cells from OT-1 transgenic mice. Bone marrow derived DC were cultured in presence of medium alone, different concentrations of synthetic SIINFEKL peptide, SIINFEKL and EDA, EDA-SIINFEKL (fusion protein) or EDA alone. Twenty-four hours later DC were harvested and used as APC in the presence of 105 non-adherent OT-1 cells. After another 24 hours, supernatant was recovered and secreted IFN-γ was measured. (B) TLR4 molecule dependency. B3Z hybridoma cells ($10^5$ cells/well) were incubated in presence of spleen cells from C57BL/6 wt mice or with splenocytes from knock out mice for TLR4 molecule ($10^5$ cells/well) and EDA-SIINFEKL protein (100 nM). (C) Cells from the spleen of C57BL76 wt mice were cocultivated with B3Z hybridoma cells and EDA-SIINFEKL protein in presence or absence of an anti-TLR4 antibody. (B and C) The quantity of IL-2 secreted to the culture supernatant was measured by a bioassay based on the use of CTLL cell line. (D) Effect of chloroquine, monensine, brefeldine or cycloheximide on antigen presentation of the fusion protein EDA-SIINFEKL. Bone marrow-derived dendritic cells were incubated for 1 hour in absence or presence of 30 mM chloroquine, brefeldine, monensine or 4 µg/ml cycloheximide, before the addition of EDA-SIINFEKL or the synthetic peptide SIINFEKL (white bars). After 10 hours in culture, said DCs were fixed in glutaraldehyde and used as antigen presenting cell (APC) ($10^4$ cells/well) in co-cultures with non-adherent OT-1 mouse cells ($10^5$ cells/well). 24 hours later, the quantity of secreted IFN-γ was measured by a commercial ELISA. To study if TLR4 expression on APC could favor the presentation process we cultured B3Z hybridoma cells (specific for SIINFEKL epitope) in the presence of spleen cells from C57BL/6 wt mice or from TLR4 KO mice, and different concentrations of EDA-SIINFEKL (nM). The amount of IL-2 released to the culture supernatant was measured by a CTLL based bioassay (FIG. 6E).

EXAMPLES

Example 1

Figure 1:
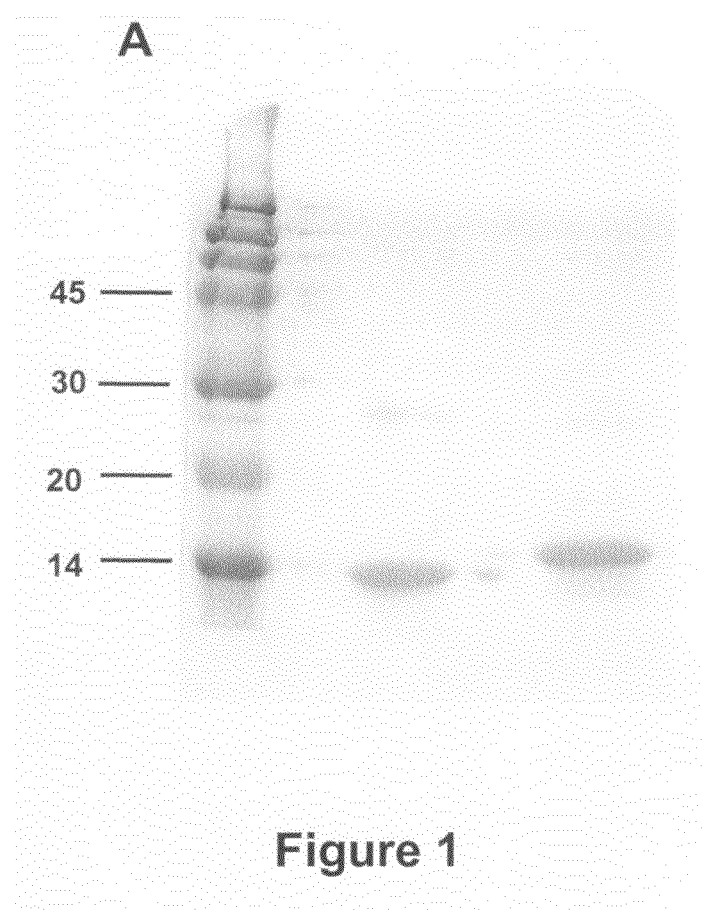
FIG. 1. SDS-PAGE analysis of produced and purified EDA and EDA-SIINFEKL proteins. One aliquot of the EDA and EDA-SIINFEKL proteins was loaded onto 15% polyacrylamide gel and subjected to electrophoresis. Molecular weight markers (MWM) are indicated in KDa. A band corresponding to the putative molecular weight of EDA and EDA-SIINFEKL proteins (13-14 KDa) is observed.

The Extra Domain A from Fibronectin Interacts with TLR4 and Activates TLR4 Signalling Pathway 1.1 Materials and Methods
1.1.1 Expression of EDA and EDA-SIINFEKL Proteinaceous Vector Recombinant Proteins
Preparation of the Recombinant Proteinaceous Vector
Fibronectin Extra domain A (EDA) was amplified by RT-PCR using specific primers and RNA from hepatocytes obtained from mice treated with concanavalin-A to induce liver damage [Lasarte et al, Hepatology. 2003; 37(2):461-70.]. Liver tissue sections were homogenized and lysed in Ultraspec (Biotecx, Houston, Tex., USA) using an Ultraturrax Driver T.25 (Janke & Kunkel, Ika-Labortechnik, Germany). RNA was isolated according to the methods of Chomczynski and Sacchi (Chomczynski P and Sacchi N. *Single-step method of RNA isolation by acid guanidinium thiocyanate-phenol-chloroform extraction. Anal Biochem* 1987; 162: 156-159). RNA was reverse transcribed (60 min at 37° C.) with 200U of M-MuLV reverse transcriptase (Gibco-BRL) in 20 µL volume of 5xRT buffer (250 mM Tris-HCl Ph 8.3, 375 mM KCl, 15 mM $MgCl_2$) supplemented with 5 mM dithiothreitol (DDT), 0.5 mM deoxynucleoside triphosphate (Boehringer Mannheim, Mannheim, Germany), 25U ribonuclease inhibitor (Promega Corporation, Madison, Wis., USA) and 200 ng random hexamers (Boehringer Mannheim). After heating (95° C., 1 min) and quick-chilling on ice, 0.3 µg of the cDNA pool was used for PCR amplification in 20 µl of 10× buffer solution (100 mM Tris-HCl pH9.3, 500 mM KCl, 1% Triton X-100) containing 0.08 mM dNTP, upstream and downstream primers (40 ng each), 1.5mM $MgCl_2$ and 2U of Taq DNA polymerase (Promega Corporation). Upstream primer was (SEQ. ID. NO: 13)

5' CCATATGAACATTGATCGCCCTAAAGCACT 3'

(the underlined bases were added to the primers to introduce a sequence recognized by the restriction enzyme NdeI whereas the sequence in italic corresponds to the beginning of EDA) and downstream primer (SEQ. ID. NO: 14)

5' AGCGGCCGCCCATTCAGTCAGTTTTTCAAAGTTGATTATACTCTCAA GCTGTGTGGACTGGATTCCAATCAGGGG 3'

(The underlined bases were added to the primers to introduce sequence recognized by the restriction enzyme NotI, the sequence in bold corresponds to sequence encoding for OVA CTL epitope (SIINFEKL) flanked by three amino acids at both ends QLESIINFEKLTEV, whereas the sequence in italic corresponds to the end of EDA).

The PCR amplified fragment was cloned in pCR2.1-TOPO using the TOPO TA cloning kit (Invitrogen, Carlsbad, Calif., USA). This plasmid was digested with NdeI and NotI and the resulting DNA fragment was subcloned in the NdeI/NotI digested plasmid pET20b (Novagen), which enables expression of fusion proteins carrying six histidine residues (6×His tags) at the carboxy terminus.

The resulting plasmid pET20b2-26 expressing the fusion protein EDA-SIINFEKL-6×His was transfected into BL21 (DE3) cells for the expression of the recombinant proteinaceous vector. Transfected cells were grown in 1 l of LB at 37° C. until OD600 reached 0.5-1. IPTG was added to the culture to a final concentration of 0.4 mM and incubated with shaking at room temperature overnignt. Cells were collected by centrifugation, resuspended in 0.1M Tris-HCl pH=7.2, treated with lysozyme, disrupted by using a French press (two passes at 20.000 pst), clarified by centrifugation and filtered. Fusion protein present in the soluble fraction was purified by affinity chromatography (Histrap, Pharmacia) by using an FPLC platform (AKTA, Pharmacia). The eluted protein was desalted using Hitrap desalting columns (Pharmacia), and concentrated using Amicon Ultra 4-5000 MWCO Centrifugal filter device (Millipore Carrighwahill, Ireland). The recombinant proteinaceous vector was purified from endotoxins by using Endotrap columns (Profos Ag, Regensburg, Germany) until the levels of endotoxin were below 0.2EU/µg protein (assessed by the LAL assay, Cambrex).

To obtain an expression plasmid for EDA protein, a PCR was performed using primers C CATATGAACATTGATCGCCCTAAAGGACT (SEQ ID NO: 13) and A GCGGCCGCTGTGGACTGGATTCCAATCAGGGG (SEQ ID NO: 15) and cloning strategies similar to those described for EDA-SIINFEKL plasmid, resulting in plasmid pET20bEDA1.2. 20 µg of protein were added to each sample in a 15% SDS-acrylamide gel, followed by staining with Coomassie blue. A band corresponding to the putative molecular weight (13 kDa) was observed.

1.1.2. Binding of EDA-SIINFEKL to TLR4. Flow Cytometry and Adhesion Assays.

To test if the recombinant EDA-SIINFEKL protein was able to bind to TLR-4 expressing cells, we used HEK293 expressing human TLR4-MD2-CD14 293 (from Invivogen). We also used HEK293 cells transfected with LacZ (Invivogen) as a negative control. Cells were pulsed with 1 mM EDA-SIINFEKL for 1 h at 4° C., washed with PBS and fixed with 4% paraformaldehyde in PBS for 10 min. After 3 washes, cells were labeled with 1/100 anti-His antibodies (Qiagen) and 1/200 anti-CD16 (FcBlock, from Becton Dickinson) for 1 hour and 30 min. After three washes, cells were incubated for 30 min with 1/100 dilution of an anti mouse IgG labeled with fluorescein and analyzed by Flow cytometry.

Alternatively, the capacity of EDA-SIINFEKL protein to inhibit FITC-stained anti-human TLR4 antibody binding to HEK-hTLR4 cells was measured. For this, HEK TLR4 cells were incubated during 2h at 4° C. in presence or absence of different dosis of EDA-SIINFEKL. Afterwards, cells were washed and incubated with anti-TLR4 antibodies and analysed by flow cytometry. Inhibition percentage was calculated for different assayed concentrations of EDA-SIINFEKL. Cell adhesion assays were also performed. HEK LacZ or HEK hTLR4 cells were previously stained with tritiated thymidine and dispensed in 96 well plates previously coated with EDA protein. After a 2-hour incubation at 37° C., non-adherent cells were removed while adhered cells were harvested and incorporated radioactivity was measured in a Topcount scintillation counter. The number of adherent cells per well was calculated with the help of standard curves obtained using different concentrations of stained cells.

1.1.3. Activation of TLR4 Signalling Pathway

Figure 3:
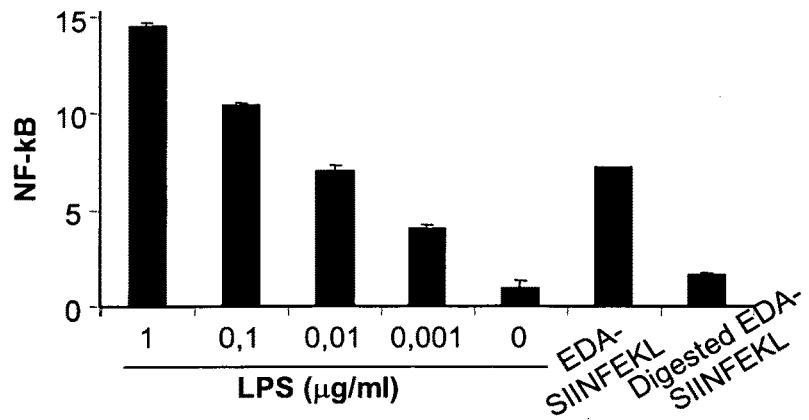
FIG. 3. EDA-SIINFEKL activates TLR4 signaling pathway. Colorimetric measurement of human secreted embryonic alkaline phosphatase gene in the culture supernatants of HEK293/TLR4-MD2-CD14 or HEK293/LacZ expressing cells transfected with this reporter gene whose expression is controlled by an NF-κB-inducible ELAM-1 promoter. 24 hours after transfection, cells were incubated in the presence or absence of different concentrations of LPS, 100 nM EDA-SIINFEKL protein (EDA), or 100 nM EDA-SIINFEKL protein previously digested with proteinase K. Bars represent NF-κB fold induction (OD obtained with supernatants from HEK293/TLR4-MD2-CD14 divided by OD obtained with supernatants from HEK293/LacZ).

HEK293/hTLR4-MD2-CD14 or HEK293/LacZ expression cells were transfected with a plasmid carrying the human secreted embryonic alkaline phosphatase gene (SEAP) according to manufacturer's instructions (Invivogen). SEAP expression is controlled by a NF-κB-inducible ELAM-1 promoter (pNiFty-SEAP (Invivogen)). Twenty four hours after transfection, cells were incubated in the presence or absence of different concentrations of LPS, 100 nM EDA-SIINFEKL protein or 100 nM EDA-SIINFEKL protein previously digested with proteinase-K. After 24 hours, expression of the reporter gene was measured in the culture supernatants by a calorimetric assay (Invivogen). In FIG. 3, bars represent the fold NF-κB induction factor (OD obtained on supernatants from HEK293/TLR4-MD2-CD14 divided by OD obtained on supernatants from HEK293/LacZ). The amount of endotoxin contaminants in EDA preparations in this assay was below 0.0003 µg/ml.

1.2 Results 1.2.1. Expression of EDA and EDA-SIINFEKL Recombinant Fusion Proteins The recombinant EDA-SIINFEKL protein was expressed in E. coli as a 6×His fusion protein (SEQ. ID. NO: 2), purified by affinity chromatography, desalted and purified from endotoxins as described in the methods section. The resulting proteins were analyzed by SDS-PAGE and western blot using anti-his antibodies (FIG. 1). A band corresponding to the putative molecular weight (13 kDa) was observed for each protein.

1.2.2. EDA-SIINFEKL Fusion Protein Binds TLR4

Figure 2:
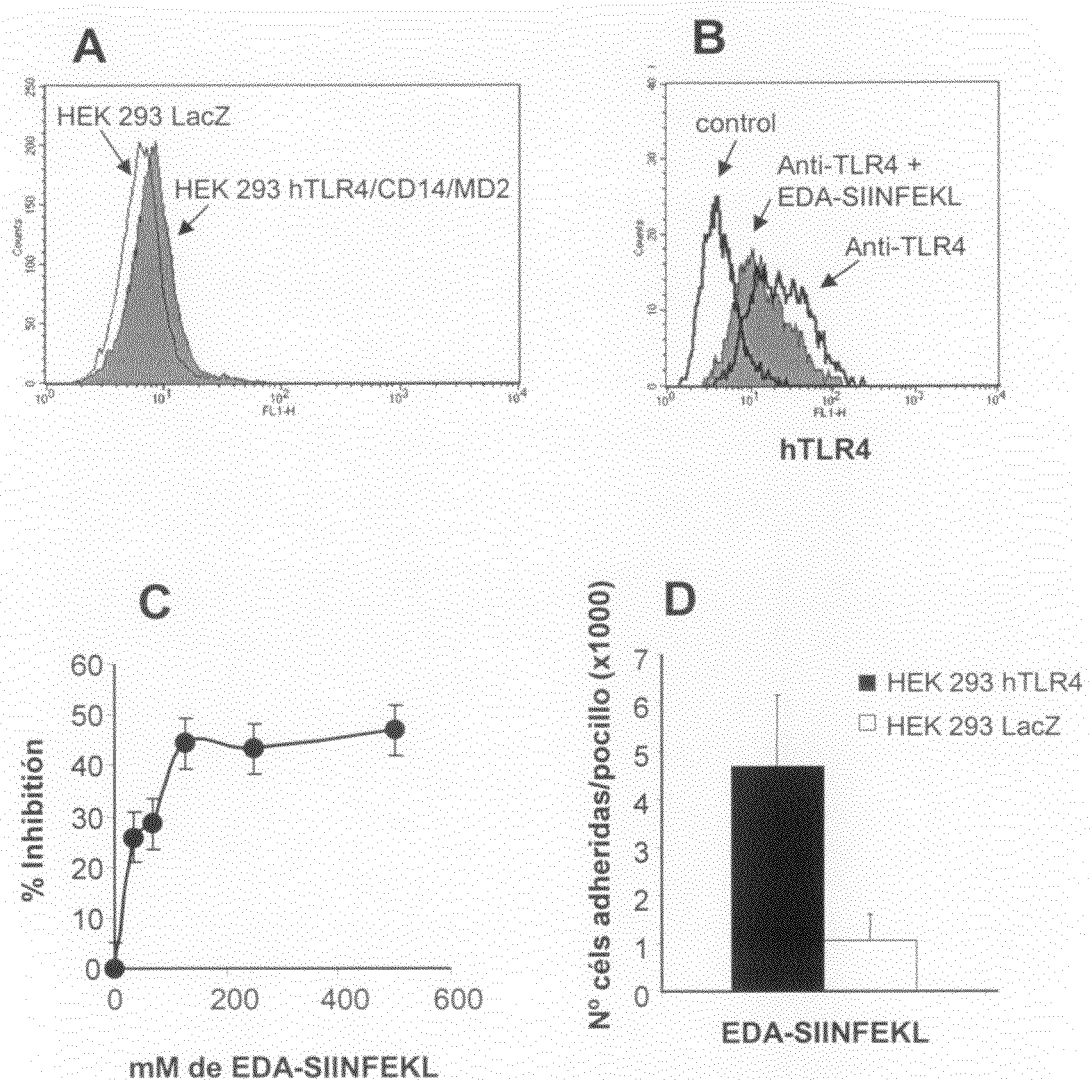
FIG. 2. Binding of the proteinaceous vector EDA-SIINFEKL to TLR4. 2A. Direct binding assays. HEK293-LacZ cells (HEK293-LacZ) and HEK293-TLR4/MD2/CD14 (HEK293-TLR4) cells were pulsed with 1 μM EDA-SIINFEKL, fixed with paraformaldehyde, labeled with anti-His and anti-EDA antibodies, developed with anti-mouse IgG-FITC and analyzed by flow cytometry. 2B. EDA capacity to inhibit binding of anti-TLR4 antibodies to TLR4 expressing cells. HEK-TLR4 cells were incubated for 2 hours at 4° C. in presence or absence of 500 nM EDA-SIINFEKL protein. Cells were washed and incubated with an anti-TLR4 antibodies stained with FITC and analysed by flow cytometry. 2C. Inhibition percentage of anti-TLR4 antibody binding to TLR4 expressing cells by means of using different concentrations of EDA-SIINFEKL protein. 2D. Cell adhesion assays. HEK-hTLR4 or HEK-LacZ cells, stained with tritiated timidine were dispensed in well of a 96-well microplate previously coated with EDA protein and incubated during 2 hours at 37° C. Non-adherent cells were eliminated whereas adherent cells were harvested and incorporated radioactivity was measured in a Topcount scintillation counter. Adherent cell numbers per well were calculated with the help of standard curves.

It has been described that fibronectin extra domain A activates Toll-like receptor 4 (Okamura et al, JBC, 2001; 276: 10229-10233). However, there is no direct evidence of physical binding of EDA to TLR4. We first analyzed whether the EDA-SIINFEKL protein has the capacity to bind cells expressing TLR4. HEK293 expressing human TLR4-MD2-CD14 or HEK293 cells transfected with LacZ (Invivogen) were pulsed with 1 µM EDA-SIINFEKL protein, labeled with anti-His antibodies and an anti-mouse IgG labeled with fluorescein (see methods) and analyzed by Flow cytometry. It was found that HEK 293 cells expressing human TLR4-MD2-CD14 presented a slightly higher fluorescence intensity than HEK 293 cells expressing LacZ (FIG. 2A). The capacity of EDA-SIINFEKL protein to inhibit fluorescein stained antibody binding to human TLR4, was also measured. The results showed that previous incubation of HEK-hTLR4 cells with 500 mM EDA-SIINFEKL protein inhibited approximately 50% of said antibody binding (FIG. 2B). FIG. 2C shows the inhibitory effect of different doses of EDA-SIINFEKL on said antibody binding. On the other hand, we measured the capacity of HEK hTLR4 and control HEK LacZ control cells to bind in an adhesion assay, to plastic wells previously coated with EDA protein. It shows that HEK hTLR4 cells are capable of specifically binding to wells that contain EDA. All these experiments indicate that EDA and EDA-SIINFEKL proteins are capable of binding TLR4.

1.2.3. EDA-SIINFEKL Fusion Protein Activates TLR4 Signalling Pathway

TLR4 signaling leads to NF-κB translocation, a transcription factor which binds to consensus elements within the promoters of a variety of genes. To determine whether recombinant EDA-SIINFEKL protein can activate TLR4, we used HEK293/hTLR4-MD2-CD14 or HEK293/LacZ cells transfected with a plasmid carrying human secreted embryonic alkaline phosphatase gene (SEAP) under the control of an NF-κB-inducible ELAM-1 promoter (pNiFty-SEAP (Invivogen)). We found that EDA-SIINFEKL protein was able to stimulate the expression of SEAP only in HEK293/hTLR4-MD2-CD14 transfected cells, reaching a fold NF-κB induction factor of 7, similar to that found when cells were incubated with 0.01 µg of LPS (FIG. 3). This capacity to stimulate NF-κB nuclear translocation was completely abrogated if EDA-SIINFEKL protein was previously digested with proteinase K (FIG. 3), suggesting that EDA activation of TLR4 cannot be accounted for by potential LPS contamination in the recombinant protein preparation.

1.3 Discussion.

We constructed the recombinant plasmid pET20b2-26 which allowed the expression of recombinant fusion protein EDA-SIINFEKL 6×His in E. coli. The presence of 6 histidines facilitates the detection and purification of the fusion protein. Thus, we were able to purify from the cytoplasmic fraction of E. coli cultures considerable amounts of the fusion protein. Binding assays carried out on TLR4 expressing cells suggested that EDA-SIINFEKL protein is able to bind TLR4 specifically. In addition, we show here that EDA-SIINFEKL is able to activate the TLR4 signaling pathway. This activation is not related to potential LPS contamination of the protein, since previous digestion with proteinase K completely abrogates the capacity to stimulate NF-κB nuclear translocation. Moreover, the amount of endotoxin contaminants in EDA preparation in this assay was below 0.0003 µg/ml (as assessed by the LAL assay) which is unable to activate TLR-4 signaling pathway in this in vitro assay. These results suggest that EDA protein could be used as a proteinaceous vehicle to target antigens to TLR4 expressing cells. Dendritic cells are known to express toll like receptors and particularly TLR4. It is also known that some of the most potent maturation stimuli for DC come from the interaction of TLR receptors with their respective ligands. Thus, interaction of a fusion protein containing EDA and a certain antigen could favour the rapid activation of innate immunity by inducing production of proinflammatory cytokines and up-regulation of costimulatory molecules. In addition, the targeting of this fusion protein to the surface of the DC could increase the capture and endocytosis of the antigen by DC and consequently enhance the immune response against this antigen.

Example 2

EDA Containing Fusion Proteins Induce Dendritic Cell Maturation In vitro and In vivo and Allow the Induction of Cytotoxic T Lymphocytes 2.1 Materials and Methods.
2.1.1. Bone Marrow Derived Dendritic Cell Generation.

Dendritic cells were grown from bone marrow cells. After lysing erythrocytes with ACK lysis buffer, cells were washed and subsequently depleted of lymphocytes and granulocytes by incubation with a mixture of antibodies against CD4 (GK1; ATCC, Manassas, Va.), CD8 (53.6.72; ATCC), Ly-6G/Gr1 (BD-Pharmingen; San Diego Calif.) and CD45R/B220 (BD-Pharmingen) followed by rabbit complement. Remaining cells were grown at $10^6$ cells/ml in 12-well plates in complete medium supplemented with 20 ng/ml of mGM-CSF and 20 ng/ml of mIL-4 (both from Peprotech; London, UK). Every two days, medium was replaced with fresh medium containing cytokines. Non-adherent dendritic cells were harvested at day 7 and cultured in the presence or absence of 1 µg/ml or 15 ng/ml LPS (Sigma), EDA-SIINFEKL (500 nM) or SIINFEKL (10 µM) at 37° C. and 5% $CO_2$. In some experiments, polymyxin (10 µg/ml) was added to the cultures to inhibit the effect of endotoxin contaminants. After 24 h culture, supernatants were harvested and IL-12 and TNF-α were measured by ELISA (BD-Pharmingen), according to manufacturer's instructions.
2.1.2 Measurement of In vivo Maturation of CD11c Cells after Immunization with EDA-SIINFEKL. Effect of Digestion with Proteinase-K.

Maturation of DC was evaluated in vitro by flow cytometry measuring the expression of various surface markers. C57BL6 mice were injected i.v. with 25 µg EDA-SIINFEKL, 25 µg EDA-SIINFEKL digested with proteinase K, 25 µg LPS or with PBS alone. Digestion of EDA-SIINFEKL with proteinase K was carried out by using agarose-proteinase K (Sigma, St Louis). Briefly, 5 mg/ml of proteinase agarose beads washed in washing buffer (20 mM Tris-HCl, pH 7.2, 1 mM EDTA, 1 mM $ClCa_2$) were used to digest EDA-SIINFEKL protein or LPS for 20 min at 30° C. Agarose-proteinase K beads were removed by centrifugation. Fifteen hours after immunization, mice were sacrificed and CD11c cells purified by autoMACS. Cells were labelled and analyzed by flow cytometry.
2.1.3. In vitro Studies to Analyse Antigen Presentation Capacity.

We characterized the ability of EDA-SIINFEKL to be captured by APC to present the processed CTL epitope SIINFEKL to T cells from OT-1 transgenic mice, or to the T hybridoma B3Z, both specific for this epitope. Bone marrow derived DC were cultured in presence of different concentrations of EDA-SIINFEKL, EDA and SIINFEKL (not covalently bound) or SIINFEKL. After twenty-four hours of culture, supernatants were collected and IFN-γ production was measured by ELISA. Alternatively, 12 hours after the initiation of the culture, DC were collected, fixed with 0.05% glutaraldehyde and used as APC in the presence of different amounts of non-adherent cells from OT-1 or in the presence of B3Z hybridoma T cell line. In some experiments DC were incubated in the presence or absence of chloroquine (3 µM), monensine (1 µl Golgystop, Pharmingen), brefeldine (1 µl Golgyplug, Pharmingen), cycloheximide (4 µg/ml), and then incubated in the presence of EDA-SIINFEKL or SIINFEKL peptide. In some cases anti-TLR4 antibody was added to the cultures.

Activation of B3Z cells in the presence of treated APC was carried out by measuring IL-2 production. B3Z hybridoma cells ($10^5$ cells/well) were cultured in complete medium (RPMI 1640 supplemented with 10% FCS, 2 mM glutamine, 100 U/ml penicillin, 100 µg/ml streptomycin and $5 \times 10^{-5}$M 2-mercaptoethanol) for 18 hours in the presence of spleen cells ($10^5$ cells/well) from C57BL/6 wt mice or from TLR4 KO mice, and different concentrations of EDA-SIINFEKL. The amount of IL-2 released to the culture supernatant was measured by a CTLL based bioassay as previously described.
2.1.4. Measurement of In vivo Induction of Cytotoxic T Lymphocytes (CTL) and IFN-γ Producing Cells after Immunization.

CS7BL6 mice were immunized i.v. with 50 µg of EDA-SIINFEKL or with SIINFEKL at days 0 and 10. At day 20, mice were sacrificed for analysis of CTL response against SIINFEKL. Splenocytes from immunized animals were cultured in the presence of 0.1 µg/ml of SIINFEKL at $5 \times 10^6$ cells/ml (10 ml) for 5 days in complete medium. On day 5, cells were harvested for chromium release assays. Lytic activity was measured by incubating for 4 h different numbers of effector cells with $1 \times 10^4$ EL-4 target cells previously loaded with $^{51}Cr$ and with or without SIINFEKL. Percentage of specific lysis was calculated according to the formula: (cpm experimental−cpm spontaneous)/(cpm maximum−cpm spontaneous)×100, where spontaneous lysis corresponds to target cells incubated in the absence of effector cells and maximum lysis is obtained by incubating target cells with 5% Triton ×100.

To measure the production of IFN-γ in response to SIINFEKL, splenocytes from immunized mice were plated on 96-well plates at $8 \times 10^5$ cells/well with complete medium alone, or with 30 µM of peptide in a final volume of 0.25 ml. Supernatants (50 µl) were removed 48 hours later and IFN-γ was measured by ELISA (Pharmingen, San Diego, Calif.) according to manufacturer's instructions.

In another group of experiments the capacity of EDA protein to act as an adjuvant in a mixture of proteins was proven. In this case, a group of C57BL/6 mice were immunised via i.v. with 50 µg of EDA-SIINFEKL in presence of 500 µg of OVA protein in PBS whereas another group was immunised with 500 µg of OVA protein alone in PBS. One week later mice were sacrificed to determine CTL response against SIINFEKL in both groups, as indicated above.
2.1.5. Protection Against EG7OVA Tumor Cell Challenge Mice were immunized s.c. on days 0 and 10 with 3 nmol of EDA-SIINFEKL or SIINFEKL. Twenty days after the second immunization mice were challenged s.c. with 105 EG7OVA cells. Tumour growth was controlled with a caliper and expressed in $mm^3$ using the formula $V=(L \times w^2)/2$, wherein L is length; w, width. Mice were sacrificed when tumor size reached a volume greater than 8 $cm^3$.
2.2. Results
2.2.1. EDA-SIINFEKL Fusion Protein Stimulates IL-12 and TNF-α Production by Bone Marrow Derived Dendritic Cells (BMDC).

Figure 4:
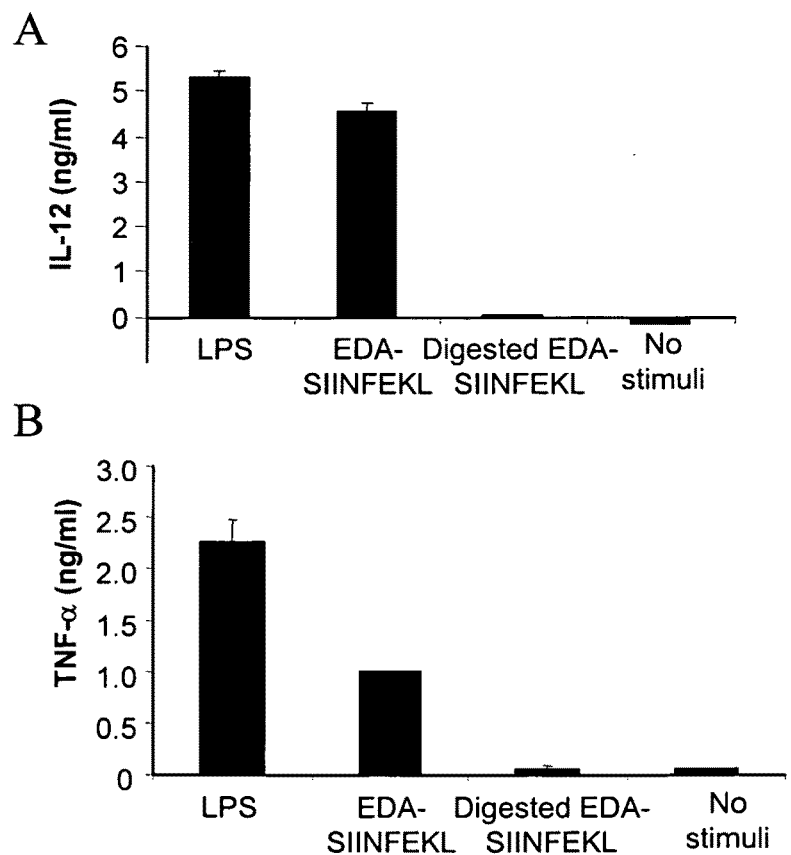
FIG. 4. EDA-SIINFEKL induces secretion of proinflammatory cytokines by DC in vitro. Bone marrow derived DC were cultured in presence of LPS (1 μg/ml), EDA-SIINFEKL (500 nM), EDA-SIINFEKL (500 nM) digested with proteinase K, or saline solution. After 24 h, presence of IL-12 (A) and TNF-α(B) were measured in culture supernatant by ELISA.

We examined whether EDA-SIINFEKL recombinant protein was able to stimulate BMDC to produce proinflammatory cytokines such as IL-12 or TNF-α. Thus, BMDC were cultured with SIINFEKL (10 µM), LPS (1 µg/ml and 15 ng/ml) or EDA-SIINFEKL-6×His (500 nM). Twenty-four hours later, IL-12 or TNF-α in the culture supernatant was measured by ELISA. It was found that EDA-SIINFEKL was able to stimulate the production of very high levels of IL-12 or TNF-α by BMDC (FIG. 4). This immunostimulatory capacity disappeared when the protein was previously treated with proteinase K, indicating that this activity wasn't due to possible traces of endotoxin in protein samples.

2.2.2. EDA-SIINFEKL induces TLR4 Dependent In Vivo Maturation of CD11c Expressing DC.

Figure 5A:
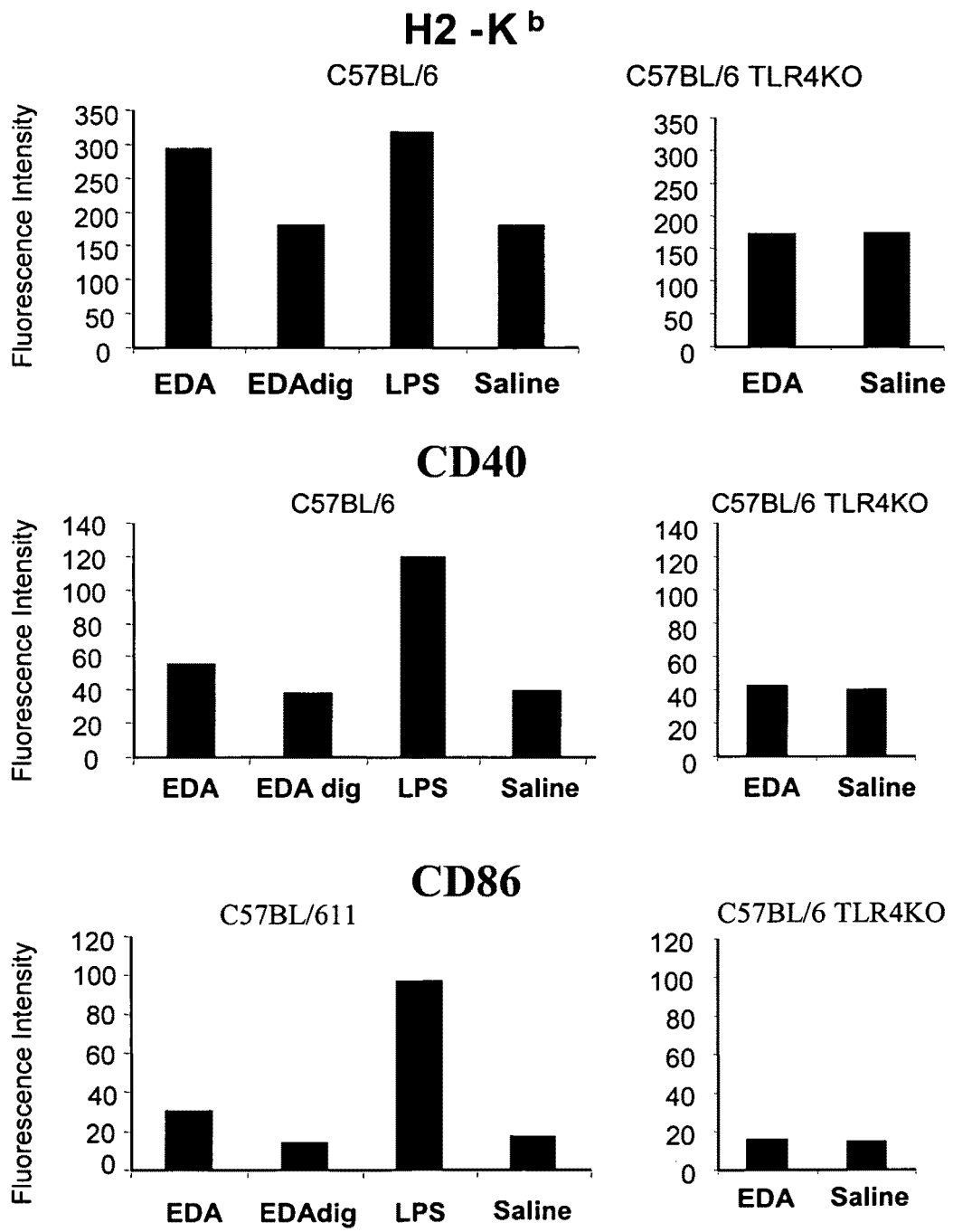
FIG. 5. EDA-SIINFEKL induces CD11c DC maturation in vivo. Maturation of dendritic cells is a requirement for the optimal stimulation of a T-cell response. When maturation occurs, APCs increase the expression of surface molecules such as class I ($H2K^b$ in our model) and class II MHC ($IA^b$ in our model), CD40, CD80 and CD86 molecules. Therefore, we analyzed whether EDA-SIINFEKL would induce maturation of CD11c expressing cells in vivo. C57BL/6 wt mice were immunized i.v. with 25 µg EDA-SIINFEKL, 25 µg EDA-SIINFEKL digested with proteinase K, 25 µg of LPS or with PBS alone. Also, C57BL/6 TLR4KO mice were immunised with 25 µg EDA-SIINFEKL or with PBS alone. Fifteen hours later mice were sacrificed and CD11c cells purified by autoMACS. Cells were labelled and analyzed by flow cytometry for expression of H-2 Kb, I-Ab, CD40, CD80 and CD86 molecules.

Dendritic cells (DC) are the most potent antigen-presenting cells with a unique ability to stimulate naive T cells and secondary responses to antigens. DC have the capacity to capture antigens, process them into peptides and present the peptides in association with MHC class I or II molecules to cytotoxic T cells (CTL) or T helper cells respectively. Immature DC can capture antigens but they must differentiate or mature to become capable of stimulating naive T cells. Thus, maturation of dendritic cells is a requirement for the optimal stimulation of a T-cell response. When maturation occurs, APCs increase the expression of surface molecules such as class I and class II MHC, CD40, CD80 and CD86 molecules. Therefore, we analyzed whether EDA-SIINFEKL could induce the maturation of CD11c expressing cells in vivo. C57BL6 mice were immunized i.v. with 25 µg EDA-SIINFEKL, 25 µg EDA-SIINFEKL digested with proteinase K, 25 µg LPS or with PBS alone. Fifteen hours later mice were sacrificed and CD11c cells purified by autoMACS, antibody labelled and analyzed by flow cytometry. We found that immunization with EDA-SIINFEKL was able to induce the expression of MHC class I and class II molecules, CD40 and CD86. This capacity of EDA-SIINFEKL was completely abrogated when the protein was digested with proteinase K before immunization (FIG. 5). Digestion of LPS with proteinase K did not have any inhibitory effect on the capacity of LPS to induce the expression of these maturation markers (not shown). We tested the capacity of EDA-SIINFEKL to induce maturation of CD11c cells from C57BL/6 TLR4 KO mice and we found that EDA-SIINFEKL was unable to induce overexpression of maturation markers found on C57BL/6 wt mice (FIG. 5).

2.2.3 EDA-SIINFEKL is Efficiently Presented by Dendritic Cells to T Cells Specific for SIINFEKL Epitope.

We characterised the ability of EDA-SIINFEKL to be captured by APC to present the processed CTL epitope SIINFEKL to T cells from OT-1 transgenic mice, specific for this epitope. Bone marrow derived DC ($10^5$ cells/well) were cultured in presence of different concentrations of EDA-SIINFEKL, EDA+SIINFEKL, EDA or SIINFEKL peptide. Forty-eight hours later, $10^5$ non-adherent OT-1 cells were added. IFN-γ production by OT-1 non-adherent cells was measured (FIG. 6A). SIINFEKL peptide was efficiently presented to T cells from OT-1 mice as proven by IFN-γ production. EDA-SIINFEKL also induces high levels of IFN-γ, although high doses of the protein are necessary to obtain levels similar or even higher of IFN-γ, clearly indicating that EDA protein carries this SIINFEKL epitope to MHC class I molecules. The addition of EDA protein to DC incubated with SIINFEKL peptide didn't increase IFN-γ production by T cells from OT-1 mice. As expected, DC incubated with EDA alone didn't activate T cells from OT-1 mice. To analyse if TLR4 molecule expression in DC could enhance EDA-SIINFEKL presentation, SIINFEKL specific B3Z cells were incubated with different concentrations of EDA-SIINFEKL in presence of spleen cells from C57BL/6 wt or TLR4KO mice. EDA-SIINFEKL presentation to B3Z cells was more efficient in presence of antigen presenting cells that expressed TLR4 (FIG. 6B). Also, EDA-SIINFEKL presentation to B3Z cells was completely blocked by addition of anti-TLR4 antibodies (FIG. 6C), suggesting that TLR4 is involved in EDA-SIINFEKL capture. Afterwards, we studied the effect of different drugs on the processing of EDA-SIINFEKL and we found that this presentation was totally inhibited by monensine, brefeldine or cycloheximide but not by chloroquine, a known inhibitor of acidification in endosomes and late lysosomes (FIG. 6D). As expected, presentation of SIINFEKL synthetic peptide was not affected by these drugs. These data suggest that internalization of EDA-SIINFEKL is not mediated by macropinocytosis and demonstrate that EDA-SIINFEKL is processed via the class I cytosolic processing pathway.

2.2.4. EDA-SIINFEKL Induces SIINFEKL Specific CTL in vivo.

Figure 7:
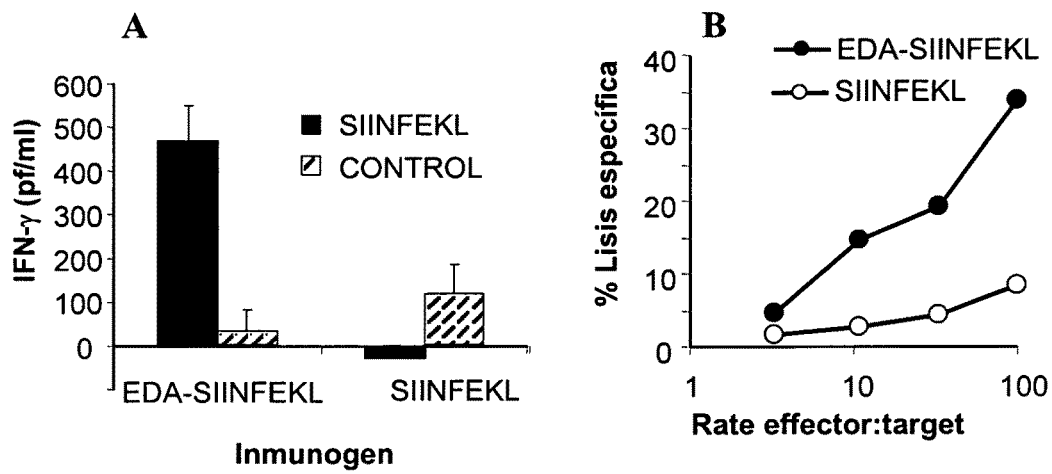
FIG. 7. Immunization of mice with EDA-SIINFEKL induces a cell response specific to SIINFEKL epitope. The preceding results demonstrate that EDA-SIINFEKL recombinant protein is bioactive and specifically activates APCs. The induction of specific T cell immune responses in vivo is critical for the development of a vaccine. Thus, we tested whether mice immunized with EDA-SIINFEKL fusion protein developed specific cell responses against this epitope. (A) Induction of IFN-γ producing cells. On days 0 and 10, C57BL/6 mice were immunized with 1.5 nmol of EDA-SIINFEKL or with 1.5 nmol of SIINFEKL peptide. On day 20, spleen cells were incubated for 48 hours in the presence or absence of SIINFEKL, and the quantity of secreted IFN-γ was measured by ELISA. (B) Induction of SIINFEKL-specific CTL response analysis. Splenocytes from mice immunized with EDA-SIINFEKL or with SIINFEKL were restimulated during 5 days in presence of SIINFEKL peptide. After this incubation CTL activity against EL-4 target cells was measured, in absence or presence of SIINFEKL peptide by a conventional chromium$^{51}$ liberation assay. The data represent the mean percentages of the values of net specific lysis (% lysis of a target cell pulsed with SIINFEKL minus the % of lysis of a non-pulsed target cell) from triplicate samples.
Figure 9:
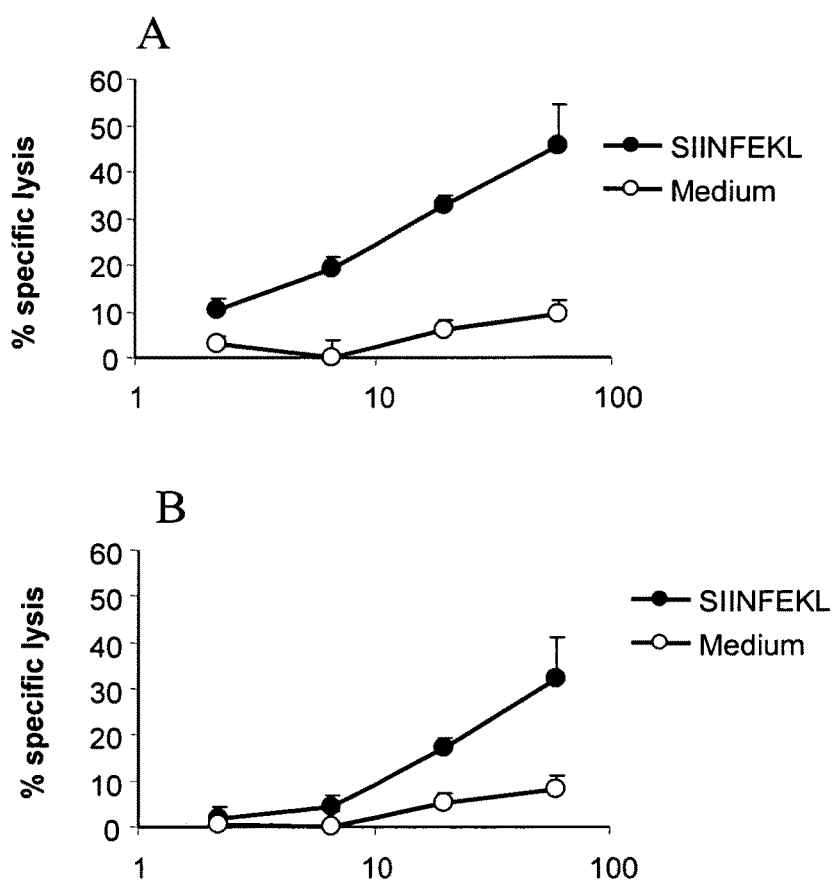
FIG. 9. EDA acts as an adjuvant in the induction of cytotoxic responses after immunization with OVA protein. There exists the possibility that if EDA is capable of promoting the maturation of dendritic cells in vivo, it may act as an adjuvant agent after immunization with a protein containing the cytotoxic epitope, but be incapable of activating a cytotoxic response by itself. To test this possibility, we immunized a group of mice with 50 µg of EDA with 500 µg of OVA protein (A) and another group of mice with 500 µg of OVA (B), without using any other type of adjuvant. One week after immunization, mice were sacrificed and splenocytes were cultivated in presence of SIINFEKL synthetic peptide. After 5 days in culture, the cytotoxic response to EL-4 target cells pulsed with SIINFEKL peptide was measured in a conventional Cr$^{51}$ liberation assay.

The preceding results demonstrate that EDA-SIINFEKL recombinant protein is bioactive and specifically activates APCs. The induction of specific T lymphocyte immune responses in vivo is critical for the development of a vaccine. Thus, we tested whether mice immunized with EDA-SIINFEKL fusion protein developed specific CTL responses against target cells pulsed with SIINFEKL epitope. C57BL6 mice were immunized i.v. with 50 µg of EDA-SIINFEKL or with SIINFEKL in PBS at days 0 and 10. On day 20, mice were sacrificed for analysis of CTL response against SIINFEKL. It was found that EDA-SIINFEKL was able to induce CTL against EL-4 target cells pulsed with SIINFEKL. On the other hand, no CTL activity was found when mice were immunized with SIINFEKL alone (FIG. 7). Due to the ability of EDA to induce in vivo maturation of dendritic cells, EDA ability to act as an adjuvant was also analysed when immunised with OVA protein. In this experiment we observed that EDA presence in the immunisation mixture has an immunostimulatory effect and is capable of enhancing CTL response induction against SIINFEKL induced by OVA protein (compare lytic activity between panels A and B of FIG. 9).

2.2.5. EDA-SIINFEKL Protects Mice from Challenge with Tumour Cells Expressing OVA Protein.

Figure 8:
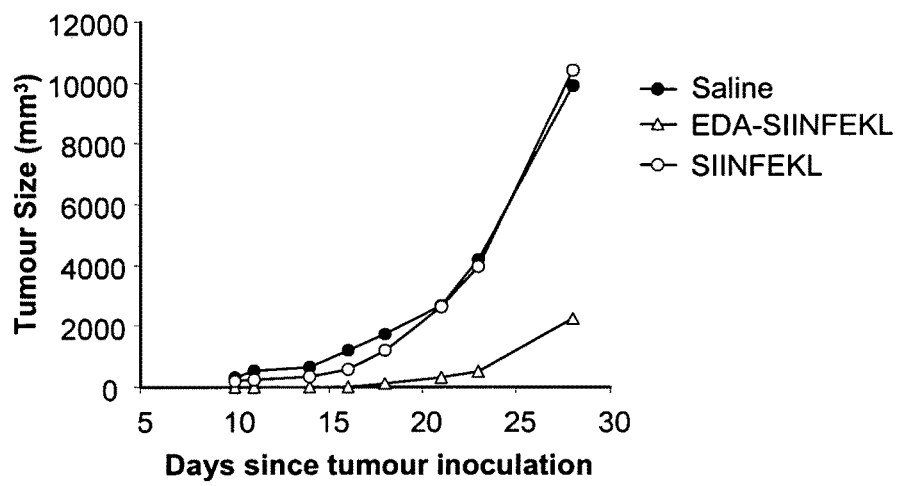
FIG. 8. EDA-SIINFEKL protects from tumor challenge with EG7 OVA expressing cells. To study the capacity of EDA-SIINFEKL fusion protein to protect mice against injection of EG7OVA tumor cells, mice were immunized s.c. at days 0 and 10 with 3 nmol of EDA-SIINFEKL, SIINFEKL or with saline solution. Twenty days after the second immunization mice were challenged s.c. with $10^5$ EG7OVA cells. Tumor growth was monitored using a caliper and expressed in cubic millimeters using the formula $V=(L \times w^2)/2$, where L, length; w, width. Mice were sacrificed when tumor size reached a volume greater than 8 cm$^3$.

To study the capacity of EDA-SIINFEKL fusion protein to protect mice against injection of EG7OVA tumour cells, mice were immunized s.c. with 3 nmol of EDA-SIINFEKL, SIINFEKL or with saline. Twenty days after the second immunization mice were challenged s.c. with 105 EG7OVA cells. We found that EDA-SIINFEKL immunization protects mice from tumour growth. All mice immunized with SIINFEKL or with saline developed tumours, whereas 40% of mice immunized with EDA-SIINFEKL remained free of tumours and the remaining 60% experimented tumour growth retardation (FIG. 8).

2.3. Discussion.

In the present study, using recombinant EDA protein as an epitope-delivery vector, we established a strategy for immunization that primes CTL responses in vivo, bypassing the need of an adjuvant. We identified the mechanisms that contribute to the efficiency of EDA containing fusion proteins as a vector to deliver antigens to TLR-4 expressing cells and to induce cellular immune responses against an antigen.

First we found that in vitro stimulation of BMDC with EDA was able to stimulate the production of proinflammatory cytokines such as IL-12 and TNF-α. These cytokines are known to be crucial for the initiation of a strong immune response against an antigen. In addition, it was found that in vivo immunization with EDA was able to induce maturation of DC and increase expression of costimulatory molecules on the surface of DC. Expression of these costimulatory molecules is of paramount importance for the efficient induction of immune responses against an antigen. It was found that this effect is dependent on the presence of TLR4, since in vivo isolated CD11c cells from C57BL/6 TLR4 KO mice previously immunized with EDA, did not show any improvement on its maturation status in comparison to that found in non immunized animals.

We found that the presence of TLR4 molecule on APC improves antigen presentation after incubation with EDA-SIINFEKL fusion protein and that this presentation was not affected by chloroquine, which inhibits endolysosomal proteolysis. These data suggest that internalization of EDA-SIINFEKL is not mediated by macropinocytosis and demonstrate that recombinant EDA-SIINFEKL protein is processed as a cytosolic antigen, and implies that the fusion protein has to be delivered to the cytosol through the APC plasma membrane.

And most importantly, we have found that immunization of mice with the recombinant fusion protein EDA-SIINFEKL is able to induce in vivo a CTL response specific against SIINFEKL epitope. Moreover, immunization with EDA-SIINFEKL is able to protect mice against challenge with EG7OVA tumor cells. All these data show that this proteinaceus vector containing EDA is able to: (i) target antigens to TLR4 expressing cells and in particular professional APC; (ii) deliver the vectorised antigen to the classical Class-I antigen processing pathway; (iii) induce dendritic cell maturation in vivo and in vitro; and (iv) prime CTL in vivo against the vectorised antigen in absence of adjuvant and thus, may be used in vaccination strategies against infectious agents or against cancer. Also, these fusion proteins containing EDA may serve for the cytosolic delivery of pharmaceutically-relevant molecules to TLR4 expressing cells. Additionally, the ability of EDA for inducing in vivo maturation of dendritic cells allows its use as an adjuvant in formulations containing an antigen against which one wants to produce an immunogenic response, opening the spectrum of possibilities for the use of EDA in vaccine development.

Example 3

EDA Protein May be Used as a Vehicle to Transport Antigens of at Least 390 Amino Acids 3.1 Materials and Methods.
3.1.1 Expression of EDA-OVA and EDA-NS3 Recombinant Proteins.

For the construction of an EDA-OVA expression plasmid, mRNA was extracted from EG7OVA tumour cells, that express OVA protein. After reverse transcription and amplification by PCR with primers GCGGCCGCAATGGGCTCCATCGGCGCA (SEQ ID NO: 16) and GCGGCCGCAGGGGAAACACATCT (SEQ ID NO: 17) (underlined bases were added to introduce the sequence recognised by restriction enzyme NotI, whereas the sequence in italics belongs to the beginning and end of ovalbumin). The PCR product was cloned in pCR2.1-TOPO using the TOPO TA kit (Invitrogen), digested with NotI and subcloned in plasmid pET20EDA 1.2 (that expresses EDA protein) previously digested with NotI. Correct orientation of the construction was verified by sequencing. After induction of *E. coli* transformed with the plasmid cultures, fusion protein present in the soluble fraction was purified by affinity chromatography (Histrap, Pharmacia) using an FPLC platform (AKTA, Pharmacia). Protein was desalted with desalting Hitrap columns (Pharmacia), and was concentrated with the filter device by centrifugation Amicon Ultra 4-5000 MWCO (Millipore Carrighwahill, Ireland). The recombinant protein vector was purified using Endotrap endotoxin columns (Profos Ag, Regensburg, Germany), until levels of endotoxin were below 0.2 EU/µg of protein (measured by LAL assay, Cambrex). For EDA-NS3 protein construction a similar strategy was followed using primers AGCGGCCGCAGCCAC-CATGGCGCCTATCACGGCCTATTC (SEQ ID NO: 18) and AGCGGCCGCTTGCGGTACGGCCGGAGGG-GATGAGTT (SEQ ID NO: 19) that allow expression of the amino-terminal fragment of NS3 protein (amino acids 1026-1221). In contrast to EDA-OVA protein which was extracted from the soluble fraction of *E. coli* fractions, in EDA-NS3 protein case, the protein was purified from inclusion bodies previously dissolved in 8M urea. After an affinity chromatography using Histrap columns, an ionic interchange chromatography (DEAE-sepharose) was performed. The purified fraction from this second chromatography was refolded following a refolding protocol in a G25 column. Once refolded, EDA-NS3 column was desalted and purified of endotoxins using Endotrap columns (Profos, Germany).

Proteins thus purified were analysed by SDS-PAGE.
3.1.2 In vitro Studies to Evaluate Antigen Presenting Ability.

The ability of EDA-OVA to be captured by APC and subsequent presentation of CTL epitope processed SIINFEKL to T lymphocytes from OT-1 transgenic mice was evaluated. Bone marrow-derived dendritic cells ($10^5$ cells/well) were cultured in presence of different concentrations of EDA-OVA, EDA+OVA (non-covalently bound), OVA or EDA. 12h later $10^5$ cells/well of non-adherent cells from OT-1 transgenic mice were added. 24 hours from the start of the culture the supernatant was extracted for secreted IFN-γ quantification by a commercial ELISA assay.
3.1.3 Measurement of In vivo T Cytotoxic Lymphocyte (CTL) Induction and IFN-γ Producing Cells after Immunization.

C57BL6 or HHD (transgenic for HLA-A2.1 molecule) mice were immunized i.v. with 50 µg of EDA-OVA or EDA-NS3 respectively, on days 0 and 10. On day 20 mice were sacrificed to determine CTL response against SIINFEKL or against NS3 1073 peptide. Splenocytes from immunized animals were cultivated in presence of 0.1 µg/ml of SIINFEKL or of 1 µg/ml of NS3 1073 at $5\times10^6$ cells/ml (10 ml) for 5 days in complete medium. On day 5, cells were harvested for chromium liberation analysis. Lytic activity was measured incubating for 4 h different amounts of effector cells with $1\times10^4$ EL-4 target cells, previously loaded with $^{51}$Cr with or without peptide. The percentage of specific lysis was calculated according to formula (experimental cpm−spontaneous cpm)/(maximum cpm−spontaneous cpm)×100, wherein spontaneous lysis corresponds to target cells incubated in absence of effector cells, and maximum lysis is obtained incubating target cells with 5% Triton ×100.

To measure IFN-γ production in response to the different peptides, splenocytes from immunized mice were dispensed in 96 well plates, $8\times10^5$ cells/well, only with complete medium, or with 30 µM of peptides NS3 1038-1046 (SEQ ID NO: 23), 1073-1081 (SEQ ID NO: 20, CVNGVCWTV), 1169-1177 (SEQ ID NO: 22), or with 1 µg/ml of recombinant NS3 in a final volume of 0.25 ml. Supernatants (50 µl) were recovered after 48 h and IFN-γ was measured by ELISA (Pharmingen, San Diego, Calif.) according to manufacturer's instructions.
3.1.4 Protection Against Infection by vHCV 1-1031 Vaccinia Virus that Expresses Hepatitis C Virus Polyprotein.

C57BL/6 were immunized on days 1 and 10 with $1\times10^6$ bone marrow-derived dendritic cells pulsed with EDA-NS3 protein. Ten days after the second immunization, mice were infected via i.p. with $5\times10^6$ pfu of recombinant vHCV 1-1031 vaccinia virus. Three days after infection, animals were sacrificed and viral charge/mg of ovarian tissue was quantified by a plaque forming unit quantification assay based on the use of BSC-1 cell line.

3.2 Results.

3.2.1 Expression and Purification of EDA-OVA and EDA-NS3 Proteins.

Figure 10:
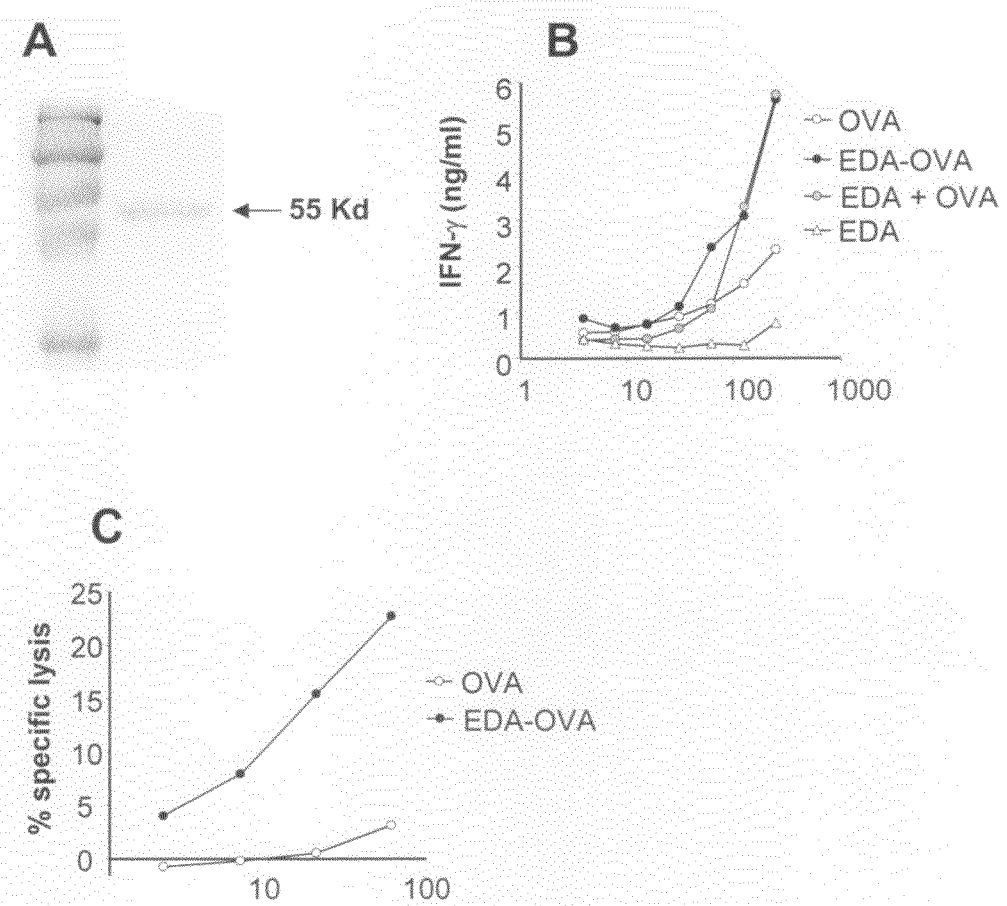
FIG. 10. EDA may act as a vehicle for larger antigens. In the previous experiments it has been proven that EDA protein may act as a vehicle to transport a cytotoxic epitope and favour induction of a CTL response against said epitope. In a later step we wanted to study if EDA was capable of transporting a larger antigen and facilitate the induction of a cellular response against said antigen. With this objective we constructed the fusion protein EDA-OVA and performed the following experiments in vitro and in vivo. (A) SDS-PAGE analysis of recombinant EDA-OVA protein. Recombinant protein EDA-OVA was expressed in E. coli, purified by affinity chromatography, desalted, detoxified, concentrated and analysed by SDS-PAGE. A band of approximately 55 kDa was observed, corresponding to the putative molecular weight of said protein. (B) Antigen presentation experiments. Bone marrow-derived DCs were cultured in presence or absence of OVA, EDA-OVA (fusion protein), EDA plus OVA, or EDA alone. 24 hours later, DCs were used as antigen presenting cells in the presence of 105 non-adherent cells from OT-1 mice. IFN-γ production by non-adherent cells from OT-1 mice in the presence of DC was quantified by a commercial ELISA. (C) EDA-OVA protein induces OVA specific CTLs in vivo. C57BL/6 mice were immunized with 1 nmol of EDA-OVA or with 1 nmol of OVA. Seven days after immunization, splenocytes from immunized mice were restimulated in vitro during 5 days in the presence of SIINFEKL peptide. Afterwards, specific CTL activity against EL-4 cells incubated in absence or presence of SIINFEKL was measured in a conventional Cr$^{51}$ liberation assay. Data represent the mean percentages of net specific lysis values (% lysis of a target cell pulsed with SIINFEKL minus % of lysis of a non-pulsed target cell) from triplicate samples.
Figure 11:
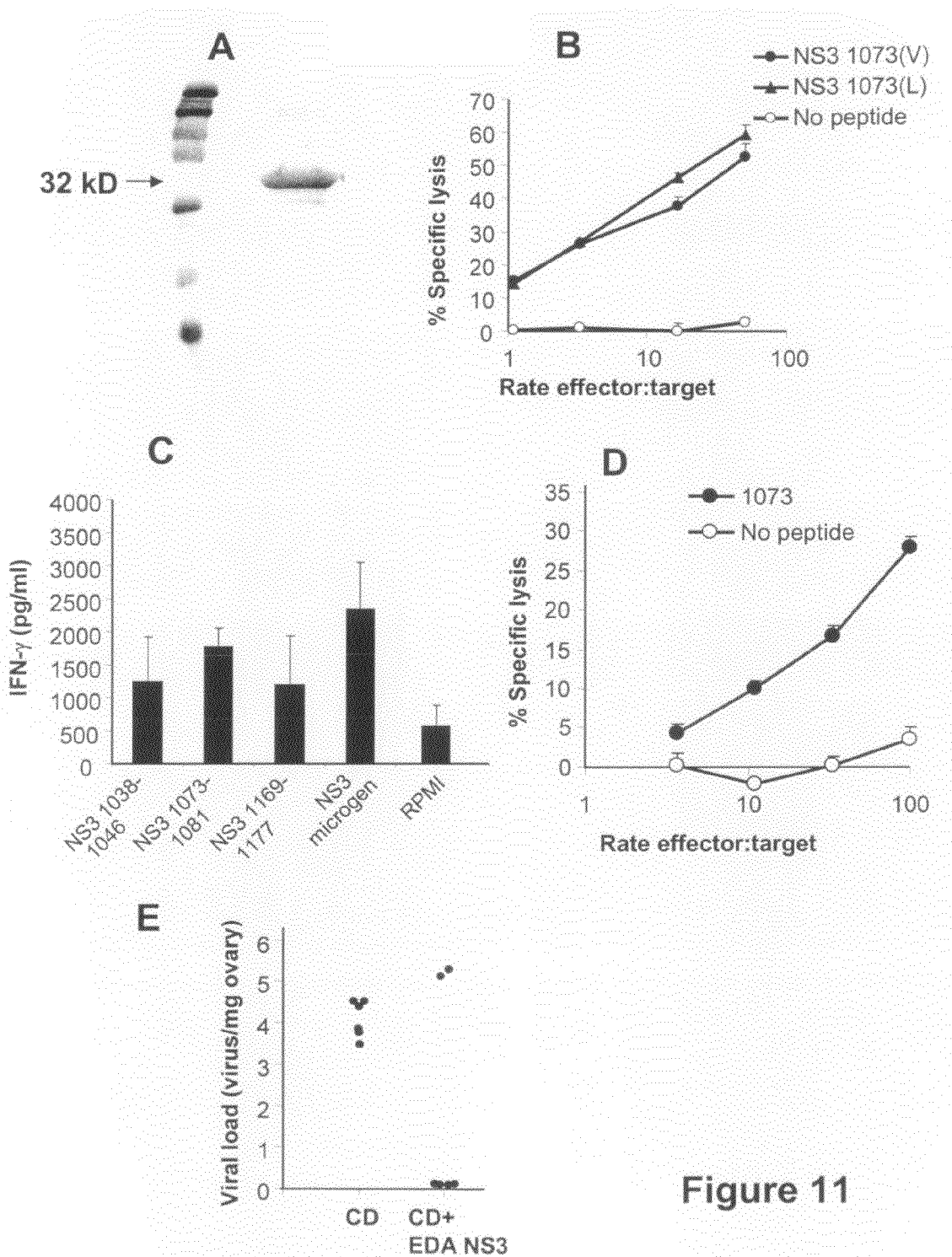
FIG. 11. EDA-NS3 protein produces a specific CTL response against NS3 hepatitis C virus protein. Having observed that EDA protein could act as a vehicle for large antigens, the capacity of EDA to induce an antiviral response to hepatitis C viral NS3 protein (amino acids 1-196 from the protease region of NS3 protein) was analysed, as a vaccination strategy against infection by said virus. (A) SDS-PAGE analysis of recombinant EDA-NS3 (1-196) protein. Recombinant fusion protein EDA-NS3 was constructed and expressed in E. coli, and analysed by SDS-PAGE. (B) EDA-OVA protein induces OVA-specific CTL in vivo. HHD mice (transgenic for HLA-A2.1 protein) were immunized, by i.v. route with 100 µg/mouse of EDA-NS3 protein dissolved in saline solution. A week after immunization, splenocytes were restimulated in vitro with NS3 1073 peptide (which contains an immunodominant cytotoxic T determinant from NS3 protein for HLA-A2 restriction). After S days in culture, cytotoxic activity was measured against T2 target cells incubated with peptide 1073(V) (SEQ ID NO: 20, CVNGVCWTV), or with 1073 (L) variant of said peptide (SEQ ID NO: 21, CLNGVCWTV) or in absence of peptide, using a conventional $Cr^{51}$ liberation assay. (C) EDA-NS3 protein induces a multiepitopic response against different epitopes from NS3 protein. Splenocytes obtained from mice immunised with EDA-NS3 were restimulated in vitro for 48 hours in the presence of peptides 1038-1046, NS3 1073-1081 or NS3 1169-1177 (that contain three cytotoxic determinants for HLA-A2 restriction within fragment 1-196 of NS3 protein) or with recombinant NS3 protein (Mikrogen). The quantity of IFN-γ secreted into the supernatant was measured by a commercial ELISA. (D) EDA-NS3 protein induces a long-lasting cytotoxic response. HHD mice were immunized by i.v. route with 100 µg/mouse of EDA-NS3 protein in saline solution. Sixty days after immunization, mice were sacrificed and presence of CTLs specific for peptide NS3 1073 was measured in a conventional chromium$^{51}$ liberation assay, using T2 target cells incubated in absence or presence of NS3 1073 peptide. (E) Immunization of C57BL/6 mice with DC incubated with EDA-NS3 protects mice from infection by recombinant vaccinia virus vHCV(1-3011) that expresses hepatitis C virus proteins. Mice were immunized with $10^6$ DC previously incubated with EDA-NS3 protein and 7 days later they received a challenge of $5×10^6$ vaccinia virus vHCV(1-3011) by i.p. route. Three days after infection mice were sacrificed and viral charge was quantified/mg of ovarian tissue, by means of a BSC-1 cell infection assay.

As indicated in Materials and methods section, EDA-OVA or EDA-NS3 were purified from transformed *E. coli* extracts using the soluble fraction in the case of EDA-OVA and form inclusion bodies in the case of EDA-NS3. In FIGS. 10A and 11A the result of SDS-PAGE for both proteins is shown. Simple bands were obtained corresponding to proteins of 55 kDa and 32 kDa sizes corresponding respectively to expected sizes for each of these proteins.

3.2.2 EDA Binding to OVA Protein Enhances Antigen Presentation of IVA to T Lymphocytes from OT-1 Transgenic Mice.

We analysed EDA binding capacity to OVA protein to enhance antigen presentation of SIINFEKL epitope to T cells specific for this epitope. We observed that bone marrow-derived dendritic cells cultured in the presence of EDA-OVA stimulated stronger IFN-γ production by non-adherent OT-1 mice cells than that induced by equimolecular amounts of OVA protein alone (FIG. 9B) We observed that IFN-γ production was also enhanced in co-cultures that contained EDA protein and OVA protein, when compared to OVA protein alone, suggesting that DC maturation induced by EDA could enhance T cell activation.

3.2.3. EDA Binding to OVA Protein or to NS3 Protein Enhances Specific Cytotoxic T Lymphocyte Induction In vivo.

The ability of EDA-OVA and EDA-NS3 to induce a CTL response against SIINFEKL epitope or against NS3 1073 epitope, respectively, was analysed. We observed, for EDA-OVA protein, that immunization with this protein dissolved in saline solution was capable of inducing a cytotoxic response against target cells incubated with SIINFEKL peptide, that immunization with OVA protein alone is not capable of inducing (FIG. 9C). In the same manner, HHD mice (transgenic for HLA-A2.1) immunization with EDA-NS3 protein induces an effective cytotoxic response against target cells previously incubated with peptide NS3 1073 (V) (SEQ ID NO: 20, CVNGNCWTV), o with variant 1073 (L) of this peptide (SEQ ID NO: 21, CLNGVCWTV) FIG. 11B. We also observed that HHD mice immunization with EDA-NS3 protein induces activation of IFN-γ producing cells specific for peptides NS3 1038 (SEQ ID NO: 23), 1073 (SEQ ID NO: 20, CVNGVCWTV) and 1169 (SEQ ID NO: 22) (FIG. 1C). Moreover, mice immunization with EDA-NS3 protein induces a long-lasting cytotoxic cellular response specific against NS3 1073 peptide. In effect, when mice immunized with EDA-NS3 protein were sacrificed 60 days after immunization, we detected the presence of CTL specific for this peptide (FIG. 11D).

3.2.4 Immunization of C57BL/6 Mice with Dendritic Cells Incubated with EDA-NS3 Protein Protects Mice Against Infection by a Vaccinia Virus that Expresses Hepatitis C Virus Proteins.

We wanted to study if immunization with dendritic cells incubated in vitro with EDA-NS3 protein was capable of inducing a cell response capable of protecting mice against challenge with a recombinant virus expressing hepatitis C virus proteins. For this reason, we immunized C57/BL6 mice with bone marrow-derived dendritic cells incubated with EDA-NS3 protein or with dendritic cells that hadn't been previously incubated with any antigen. Ten days after the second immunization, mice were infected with 5×106 pfu of recombinant vHCV 1-3011 vaccinia virus (a kind gift from Dr Rice, Washington University School of Medicine, St Louis, Mo. and described by Grakoui A, et al. J. Virol. 1993; 67:1385). Three days later viral load was measured in both groups of mice. In this experiment we observed that immunization with DC incubated with EDA-NS3 protein was capable of protecting 6% of mice against infections by recombinant vaccinia virus.

3.3. Discussion.

As has been shown in previous results, EDA protein can serve as a useful vector for targeting SIINFEKL epitope from OVA protein to TLR4 molecule expressing cells and enhance their immunogenicity. To evaluate the capacity of EDA to increase the immunogenicity of bigger proteins, we constructed EDA-OVA fusion recombinant proteins that contained complete OVA (397 amino acids) and EDA-NS3 protein that contains the fragment with protease activity of NS3 protein from hepatitis C virus.

These results demonstrate that EDA protein can act as a very efficient vector to target bigger antigens. Thus, we find that in antigen presentation assays that the binding of OVA to EDA enhances antigen capture by antigen presenting cells, increasing specific T cell activation. Also, we observed that immunization with these fusion proteins (EDA-OVA and EDA-NS3) allow the induction of specific cytotoxic responses against these antigens. These induced responses were long lasting. Finally, we observed that administration of EDA-NS3 protein with dendritic cells allows induction of a protective cellular response against the infection by vaccinia virus that expresses hepatitis C virus proteins.

These data indicate that EDA protein can be a very adequate protein vector for the induction of cellular responses against an antigen of interest. The construction of fusion proteins based on EDA protein is an appropriate strategy in vaccination protocols against tumour diseases or diseases caused by infectious agents.

The invention claimed is:

1. A proteinaceous vector which comprises a polypeptide whose amino acid sequence is selected from:
   a) fibronectin EDA domain (EDA), or
   b) a fragment of an EDA domain capable of binding TLR4,
      wherein said EDA domain consists of
      residues 2 to 91 of SEQ. ID. NO: 2,
      SEQ. ID. NO: 4,
      residues 2 to 57 of SEQ. ID. NO: 6, or
      SEQ. ID. NO: 8 bound to a molecule of interest selected from the group consisting of: a viral antigen, a fungal antigen, a parasitic antigen, a tumoral antigen, and a tumoral antigenic determinant,
   wherein the proteinaceous vector is capable of translocating the molecule of interest into a TLR4 expressing cell.

2. The proteinaceous vector according to claim 1, wherein said molecule of interest is a viral antigen.

3. The proteinaceous vector according to claim 2, wherein said molecule of interest is a viral antigen from hepatitis C virus.

4. The proteinaceous vector according to claim 3, wherein the hepatitis C viral antigen is NS3 protein or an antigenic fragment of said protein.

5. The proteinaceous vector according to claim 4, wherein said hepatitis C viral antigen consists of the amino acid sequence of SEQ ID NO: 10.

6. The proteinaceous vector according to claim 1, wherein said molecule of interest is selected from a tumoral antigen and a tumoral antigenic determinant.

7. The proteinaceous vector according to claim 1, wherein the proteinaceous vector comprises an amino acid sequence selected from the group consisting of amino acid residues 2-91 of SEQ ID NO: 2 and amino acid residues 2-57 of SEQ ID NO: 6.

8. The proteinaceous vector according to claim 1, wherein said EDA domain consists of an amino acid sequence selected from the group consisting of:

a) amino acid residues 2 to 91 of SEQ. ID. NO: 2; and b) sequence SEQ. ID. NO: 4.

9. The proteinaceous vector according to claim 1, wherein said EDA domain consists of an amino acid sequence selected from the group consisting of:

a) amino residues 2 to 57 of SEQ. ID. NO: 6; and b) sequence SEQ. ID. NO: 8.

10. The proteinaceous vector according to claim 1, wherein said molecule of interest is a parasitic antigen.

11. The proteinaceous vector according to claim 1, wherein said molecule of interest is a fungal antigen.

12. The proteinaceous vector according to claim 1, wherein the vector is capable of inducing a CTL response against the molecule of interest.

13. A pharmaceutical composition which comprises at least one acceptable pharmaceutical carrier, and at least one proteinaceous vector defined in claim 1.

14. The pharmaceutical composition according to claim 13, wherein the composition is a vaccine or an immunotherapeutic composition.

15. A method for stimulating an antigen-specific immune response in a human or animal subject in need thereof, comprising the administration to the subject of the proteinaceous vector bound to a molecule of interest according to claim 1.

16. The method according to claim 15, for the treatment or prophylaxis of a viral infectious disease, a fungal infectious disease, a parasitic infectious disease or a tumoral disease.

17. The method according to claim 16, wherein the disease is a viral infectious disease.

18. The method according to claim 17, wherein the viral infectious disease is hepatitis C.

19. The method according to claim 16, wherein the disease is a tumoral disease.

20. The method according to claim 15, wherein the EDA domain or the fragment of the EDA domain capable of binding TLR4 comprises a polypeptide whose amino acid sequence is selected from:

a) amino acids 2-91 of SEQ ID NO: 2;

b) SEQ ID NO: 4; and c) a fragment of sequence a) or b).

21. The method according to claim 15, wherein the EDA domain or the fragment of the EDA domain capable of binding TLR4 comprises a polypeptide whose amino acid sequence is selected from:

a) amino acids 2-57 of SEQ ID NO: 6;

b) SEQ ID NO: 8; and c) a fragment of sequence a) or b).

22. The method according to claim 15, wherein said antigen is a viral antigen from hepatitis C virus.

23. The method according to claim 15, wherein said antigen is selected from a tumoral antigen and a tumoral antigenic determinant.

24. The method according to claim 22, wherein the hepatitis C viral antigen is NS3 protein or an antigenic fragment of said protein.

25. The method according to claim 24, wherein said amino acid sequence is SEQ ID NO: 10.

* * * * *